(12) United States Patent
Fournier et al.

(10) Patent No.: US 7,935,349 B2
(45) Date of Patent: May 3, 2011

(54) CRMP4B INHIBITORY PEPTIDE

(75) Inventors: Alyson E. Fournier, Montréal (CA); Yazan Z. Alabed, Montréal (CA)

(73) Assignee: The Royal Institution for the Advancement of Learning/McGill University, Montreal (CA)

( * ) Notice: Subject to any disclaimer, the term of this patent is extended or adjusted under 35 U.S.C. 154(b) by 28 days.

(21) Appl. No.: 12/225,164

(22) PCT Filed: Mar. 19, 2007

(86) PCT No.: PCT/CA2007/000440
§ 371 (c)(1), (2), (4) Date: Sep. 16, 2008

(87) PCT Pub. No.: WO2007/106991
PCT Pub. Date: Sep. 27, 2007

(65) Prior Publication Data
US 2009/0048169 A1    Feb. 19, 2009

Related U.S. Application Data

(60) Provisional application No. 60/783,030, filed on Mar. 17, 2006.

(51) Int. Cl.
*A61K 39/00* (2006.01)
*C07K 1/00* (2006.01)
*C07K 14/00* (2006.01)

(52) U.S. Cl. ............... 424/185.1; 424/184.1; 424/192.1; 530/350

(58) Field of Classification Search ................. None
See application file for complete search history.

(56) References Cited

FOREIGN PATENT DOCUMENTS
JP    2004000094 A  *  1/2004

* cited by examiner

*Primary Examiner* — Olga N Chernyshev
(74) *Attorney, Agent, or Firm* — Ogilvy Renault LLP

(57) ABSTRACT

The present invention relates to the identification of the cytosolic phosphoprotein CRMP4b as a protein that physically and functionally interacts with RhoA to mediate neurite outgrowth inhibition. siRNA-mediated knockdown of CRMP4 promotes neurite outgrowth on myelin substrates indicating a critical role for CRMP4 in neurite outgrowth inhibition. Disruption of CRMP4b-RhoA binding with a competitive inhibitor attenuates neurite outgrowth inhibition on myelin and aggrecan substrates. Stimulation of neuronal growth cones with Nogo leads to co-localization of CRMP4b and RhoA at discrete regions within the actin-rich central and peripheral domains of the growth cone indicative of a potential function in cytoskeletal rearrangements during neurite outgrowth inhibition. Together these data indicate that a RhoA-CRMP4b complex forms in response to inhibitory challenges in the growth cone environment and regulate cytoskeletal dynamics at distinct sites necessary for axon outgrowth inhibition. Competitive inhibition of CRMP4b-RhoA binding suggests a novel, highly specific therapeutic avenue for promoting regeneration following CNS injury.

3 Claims, 12 Drawing Sheets

Rat CRMP4b Amino Acid and cDNA Sequence Data

(a) Rat CRMP4b amino acid sequence with C4RIP sequence shaded in grey (SEQ ID NO: 1)

MASGRRGWDSSHEDDLPVYLARPGTTDQVPRQKYGGMFCNVEGA

FESKTLDFDALSVGQRGAKTPRSSQGSGRGAGNRPGVEGDTRRGPGREESREPVPESP

KPAGVEIRSATGKEVLQNLGPKDKSDRLLIKGGRIVNDDQSFYADIYMEDGLIKQIGD

NLIVPGGVKTIEANGKMVMPGGIDVHTHFQMPYKGMTTVDDFFQGTKAALAGGTTMII

DHVVPEPESSLTEAYEKWREWADGKSCCDYALHVDITHWNDSVKQEVQNLSKEKGVNS

FMVYMAYKDLYQVSNTELYEIFTCLGELGAIAQVHAENGDIIAQEQARMLEMGITGPE

GHVLSRPEELEAEAVFRAITVASQTNCPLYVTKVMSKSAADLISQARKKGNVVFGEPI

TASLGIDGTHYWSKNWAKAAAFVTSPPLSPDPTTPDYINSLLASGDLQLSGSAHCTFS

TAQKAIGKDNFTAIPEGTNGVEERMSVIWDKAVATGKMDENQFVAVTSTNAAKIFNLY

PRKGRIAVGSDSDLVIWDPDAVKIVSAKNHQSVAEYNIFEGMELRGAPLVVICQGKIM

LEDGNLHVTQGAGRFIPCSPFSDYVYKRIKARRKMADLHAVPRGMYDGPVFDLTTTPK

GGTPAGSTRGSPTRPNPPVRNLHQSGFSLSGTQVDEGVRSASKRIVAPPGGRSNITSL
S

(b) Rat C4RIP Amino Acid Sequence (SEQ ID NO: 2)

MASGRRGWDSSHEDDLPVYLARPGTTDQVPRQKYGGMFCNVEGA

FESKTLDFDALSVGQRGAKTPRSSQGSGRGAGNRPGVEGDTRRGPGREESREPVPESP

KPAGVEIRSATGKEVLQNLGPKDK

(c) Rat CRMP4b cDNA sequence with C4RIP coding region shaded in grey (SEQ ID NO: 3)

```
  1 atggcttcgg gccgaagggg ttgggacagc tcccacgagg acgacctgcc tgtgtacttg
 61 gcccggccgg tgaccacaga cgagtcccg ggcacaaat acggtggcat gttctgcaag
121 gtggaggggc cttcgagag caagacattg gatttcgatg ccctgagtgt ggagcagcgc
181 ggcgccaaaa ctccccggag cagccaggg agcggccgcg gcggggaa ccggcccggg
241 gtggaaggg acacggaac gtccgggc ccaggcgcc gcgaagagt ccgagaccg
301 tcgcccaagc ccgcgggcg tagagatcgg agcgccactg gcaaggagt tctgcagaac
361 ctggtcccta aggacaagag tgaccgtctt ctaatcaagg gagggagaat cgtcaacgat
421 gatcagtcct tttatgctga tatttacatg gaggatggct tgataaagca aattggagac
481 aatctgattg tccctggagg tgtgaagacc attgaggcca tgggaagat ggtgatgcct
541 ggaggcattg atgtccatac ccacttccag atgccttaca agggatgac cacagtggac
601 gatttcttcc aagggacaaa ggctgcctta gcgggaggaa ccaccatgat cattgaccat
661 gtggtacctg aacctgagtc tagcctgacc gaggcctatg aaaagtggcg tgagtgggct
```

Figure 9

```
721  gacgggaaga gctgctgtga ctatgctttg catgtggaca tcacccactg gaatgacagc
781  gtcaagcaag aggtgcagaa cctcagtaag gaaaaggcg ttaactcctt catggtttac
841  atggcataca aggatttata tcaagtgtcc aacacagagc tctatgagat cttcacctgc
901  ctgggagaac tgggggccat tgctcaagtt catgccgaga atggagacat cattgcccag
961  gagcaggcac gaatgctgga atgggaata acaggcccag aagtcatgt tctgagcaga
1021 ccggaagagc tggaagctga ggctgtgttc cgtgccatca ccgtcgccag ccagaccaac
1081 tgccccnttt atgtcaccaa ggtcatgagc aagagcgcgg ctgatctcat ctcacaagcc
1141 aggaagaaag gaaatgtggt ctttggcgag cccatcactg ccagcctggg aatagatgga
1201 acccattact ggagtaagaa ctgggccaag gcagctgcat ttgtgacatc cccacctctg
1261 agccctgacc caaccacacc tgactacatc aactccttgc tggccagtgg agatctgcag
1321 ctctctggaa gtgcccactg taccttcagc actgcccaga agccattgg gaaggacaac
1381 ttcacggcta tccctgaggg caccaatggc gtggaggagc gtatgtctgt catctgggac
1441 aaggctgtgg ccacagggaa gatggatgaa aaccagtttg tggctgtgac aagtaccaac
1501 gctgccaaga tattcaacct gtaccctcgc aagggagaa tagctgtggg ttctgacagc
1561 gaccttgtca tctgggatcc agatgccgtg aagatcgtct ctgccaagaa ccaccagtcg
1621 gttgcggaat acaacatctt tgaagggatg gagctgcgtg ggcacctct ggtggttatc
1681 tgccagggca agatcatgct ggaagatggt aacctgcacg tgacccaggg ggccggccgc
1741 ttcattccct gcagcccatt ctctgactat gtctataagc gcattaaagc aaggaggaag
1801 atggcggacc tgcatgcagt cccaagaggc atgtatgatg gaccagtgtt tgacttgacc
1861 accaccccca aggggggcac cccagctggc tctactcgag gctctcccac tcggccaaac
1921 ccaccagtga ggaacctcca tcagtcggga tttagtctgt caggcaccca agtggatgag
1981 ggtgtccgct cagccagcaa acgcattgtg gcgccccctg gaggccgttc taacatcaca
2041     tccctgagtt aa
```

(d) Rat C4RIP cDNA sequence (SEQ ID NO: 4)

```
1   atggcttcgg gccgaagggg ttgggacagc tcccacgagg acgacctgcc tgtgtacttg
61  gcccggccgg gcaccagaga tcaggtccca cggcagaagt acggtggcat gttctgcaac
121 gtggagggcg ccttcgagag caagacattg gattttgatg ccctgagtgt gggacagcgc
181 ggcgccaaaa ctccccggag cagccagggc agcggccgcg gcgcggggaa ccggcccggg
241 gtgaagggg acacgcgcag gggcccgggc cgggaggaga gcagggagcc cgtgcctgag
301 tcgcccaagc ccgccggggt agagatccgg agcgccactg gcaaggaggt cttgcagaac
361 ctcggtccca aggacaag
```

(e) Rat CRMP4a amino acid sequence (SEQ ID NO: 5)

MSYQGKKNIPRITSDRLLIKGGRIVNDDQSFYADIYMEDGLIKQ

IGDNLIVPGGVKTIEANGKMVMPGGIDVHTHFQMPYKGMTTVDDFFQGTKAALAGGTT

MIIDHVVPEPESSLTEAYEKWREWADGKSCCDYALHVDITHWNDSVKQEVQNLSKEKG

VNSFMVYMAYKDLYQVSNTELYEIFTCLGELGAIAQVHAENGDIIAQEQARMLEMGIT

GPEGHVLSRPEELEAEAVFRAITVASQTNCPLYVTKVMSKSAADLISQARKKGNVVFG

EPITASLGIDGTHYWSKNWAKAAAFVTSPPLSPDPTTPDYINSLLASGDLQLSGSAHC

TFSTAQKAIGKDNFTAIPEGTNGVEERMSVIWDKAVATGKMDENQFVAVTSTNAAKIF

NLYPRKGRIAVGSDSDLVIWDPDAVKIVSAKNHQSVAEYNIFEGMELRGAPLVVICQG

KIMLEDGNLHVTQGAGRFIPCSPFSDYVYKRIKARRKMADLHAVPRGMYDGPVFDLTT

TPKGGTPAGSTRGSPTRPNPPVRNLHQSGFSLSGTQVDEGVRSASKRIVAPPGGRSNI
TSLS

Figure 9

(f) Rat CRMP4a cDNA nucleotide sequence (SEQ ID NO:6)

```
   1 atgtcctacc agggcaagaa gaacattcct cggatcacga gtgaccgtct tctaatcaag
  61 ggagggagaa tcgtcaacga tgatcagtcc ttttatgctg atatttacat ggaggatggc
 121 ttgataaagc aaattggaga caatctgatt gtccctggag gtgtgaagac cattgaggcc
 181 aatgggaaga tggtgatgcc tggaggcatt gatgtccata cccacttcca gatgccttac
 241 aaggggatga ccacagtgga cgatttcttc caagggacaa aggctgcctt agcgggagga
 301 accaccatga tcattgacca tgtggtacct gaacctgagt ctagcctgac cgaggcctat
 361 gaaaagtggc gtgagtgggc tgacgggaag agctgctgtg actatgcttt gcatgtggac
 421 atcacccact ggaatgacag cgtcaagcaa gaggtgcaga acctcagtaa ggaaaaaggc
 481 gttaactcct tcatggttta catggcatac aaggatttat atcaagtgtc caacacagag
 541 ctctatgaga tcttcacctg cctgggagaa ctgggggcca ttgctcaagt tcatgccgag
 601 aatggagaca tcattgccca ggagcaggca cgaatgctgg aaatgggaat aacaggccca
 661 gaaggtcatg ttctgagcag accggaagag ctggaagctg aggctgtgtt ccgtgccatc
 721 accgtcgcca gccagaccaa ctgccccctt tatgtcacca aggtcatgag caagagcgcg
 781 gctgatctca tctcacaagc caggaagaaa ggaaatgtgg tctttggcga gcccatcact
 841 gccagcctgg aatagatgg aacccattac tggagtaaga actgggccaa ggcagctgca
 901 tttgtgacat ccccacctct gagccctgac ccaaccacac tgactacat caactccttg
 961 ctggccagtg gagatctgca gctctctgga agtgcccact gtaccttcag cactgcccag
1021 aaagccattg gaaggacaa cttcacggct atccctgagg gcaccaatgg cgtggaggag
1081 cgtatgtctg tcatctggga caaggctgtg gccacaggga gatggatga aaaccagttt
1141 gtggctgtga caagtaccaa cgctgccaag atattcaacc tgtaccctcg caaggggaga
1201 atagctgtgg ttctgacag cgaccttgtc atctgggatc cagatgccgt gaagatcgtc
1261 tctgccaaga ccaccagtc ggttgcgaa tacaacatct ttgaagggat ggagctgcgt
1321 ggggcacctc tggtggttat ctgccagggc aagatcatgc tggaagatgg taacctgcac
1381 gtgacccagg gggccggccg cttcattccc tgcagcccat tctctgacta tgtctataag
1441 cgcattaaag caaggaggaa gatggcggac ctgcatgcag tcccaagagg catgtatgat
1501 ggaccagtgt tgacttgac caccacccc aagggggca ccccagctgg ctctactcga
1561 ggctctccca ctcggccaaa cccaccagtg aggaacctcc atcagtcggg atttagtctg
1621 tcaggcaccc aagtggatga gggtgtccgc tcagccagca acgcattgt ggcgcccct
1681 ggaggccgtt ctaacatcac atccctgagt taa
```

Figure 9

Sample Membrane Translocating-Sequences with and without C4RIP a) C4RIP sequence with C3-05 MTS (SEQ ID NOS: 8 and 9)

Bam HI
▮▮▮▮▮ATGGCTTCGGGCCGAAGGGGTTGGGACAGCTCCCACGAGGACGACCTGCCTGTGTACTTGGCC
CGGCCGGGCACCACAGATCAGGTCCCACGGCAGAAGTACGGTGGCATGTTCTGCAACGTGGAGGGCGCC
TTCGAGAGCAAGACATTGGATTTTGATGCCCTGAGTGTGGGACAGCGCGGCGCCAAAACTCCCCGGAGC
AGCCAGGGCAGCGGCCGCGGCGCGGGGAACCGGCCCGGGGTGGAAGGGGACACGCGCAGGGGCCCGGGC
CGGGAGGAGAGCAGGGAGCCCGTGCCTGAGTCGCCCAAGCCCGCCGGGGTAGAGATCCGGAGCGCCACT
GGCAAGGAGGTCTTGCAGAACCTCGGTCCCAAGGACAAG▮▮▮▮GTGATGAATCCCGCAAACGCGCAA
GGCAGACATACACCCGGTACCAGACTC▮▮▮▮         Eco RI     C3-05
permeability sequence
             Xho I MASGRRGWDS SHEDDLPVYL ARPGTTDQVP RQKYGGMFCN VEGAFESKTL DFDALSVGQR
GAKTPRSSQG SGRGAGNRPG VEGDTRRGPG REESREPVPE SPKPAGVEIR SATGKEVLQN
LGPKDKEFVM NPANAQGRHT PGTRLL b) C3-05 MTS (SEQ ID NO: 10)

GTGATGAATCCCGCAAACGCGCAAGGCAGACATACACCCGGTACCAGACTC c) C4RIP sequence with Kaposi MTS (SEQ ID NOS: 11 and 12)

Bam HI
▮▮▮▮▮ATGGCTTCGGGCCGAAGGGGTTGGGACAGCTCCCACGAGGACGACCTGCCTGTGTACTTGGCC
CGGCCGGGCACCACAGATCAGGTCCCACGGCAGAAGTACGGTGGCATGTTCTGCAACGTGGAGGGCGCC
TTCGAGAGCAAGACATTGGATTTTGATGCCCTGAGTGTGGGACAGCGCGGCGCCAAAACTCCCCGGAGC
AGCCAGGGCAGCGGCCGCGGCGCGGGGAACCGGCCCGGGGTGGAAGGGGACACGCGCAGGGGCCCGGGC
CGGGAGGAGAGCAGGGAGCCCGTGCCTGAGTCGCCCAAGCCCGCCGGGGTAGAGATCCGGAGCGCCACT
GGCAAGGAGGTCTTGCAGAACCTCGGTCCCAAGGACAAG▮▮▮▮GCAGCCGTTCTTCTCCCTGTTCTT
CTTGCCGCACCC▮▮▮▮         Eco RI    mts kaposi
permeability sequence
Xho I ASGRRGWDS SHEDDLPVYL ARPGTTDQVP RQKYGGMFCN VEGAFESKTL DFDALSVGQR
GAKTPRSSQG SGRGAGNRPG VEGDTRRGPG REESREPVPE SPKPAGVEIR SATGKEVLQN
LGPKDKEFAA VLLPVLLAAP LE d) Kaposi MTS (SEQ ID NO: 13)

GCAGCCGTTCTTCTCCCTGTTCTTCTTGCCGCACCC

CRMP4B INHIBITORY PEPTIDE

CROSS-REFERENCE TO RELATED APPLICATIONS

This application claims the benefit of U.S. Provisional Application No. 60/783,030 filed on Mar. 17, 2006, which is hereby incorporated by reference in its entirety.

FIELD OF THE INVENTION

The present invention relates to a novel application in the field of neurobiology. More specifically, the present invention concerns the discovery of a novel CRMP4-RhoA interaction and its role in myelin inhibition. It has been found that specific disruption of this CRMP4-RhoA interaction circumvents myelin-dependent inhibition of neuron regeneration. Modulation of the CRMP4-RhoA interaction and of CRMP4 activity may be useful for a number of applications, including the repair of injured central nervous system (CNS) or peripheral nervous system (PNS) axons. A specific CRMP4-RhoA complex antagonist has been identified that renders neurons insensitive to myelin-dependent neurite outgrowth inhibition.

BACKGROUND OF THE INVENTION

Trauma in the adult mammalian central nervous system (CNS) results in devastating clinical consequences due to the failure of injured axons to spontaneously regenerate. Chondroitin sulphate proteoglycans (CSPGs) and the myelin-associated inhibitors (MAIs) myelin-associated glycoprotein (MAG) (McKerracher et al., 1994; Mukhopadhyay et al., 1994), Nogo-A (Chen et al., 2000; GrandPre et al., 2000; Prinjha et al., 2000) and Oligodendrocyte-myelin glycoprotein (OMgp) (Kottis et al., 2002; Wang et al., 2002) bind receptor molecules on injured axons initiating intracellular signaling cascades which block axonal regrowth (Mandemakers and Barres, 2005). In part, CSPGs and MAIs inhibit axon regeneration by disrupting Rho-GTPase-dependent cytoskeletal dynamics. Blockade of RhoA and a downstream effector Rho kinase (ROCK) promotes axon regeneration both in vitro and in vivo (Dergham et al., 2002; Borisoff et al., 2003; Fournier et al., 2003); however, the ability of RhoA and ROCK to affect multiple physiological processes in many cell types (Riento and Ridley, 2003) highlights the need to identify novel intracellular signaling substrates of neurite outgrowth inhibition to develop more specific and potent therapeutic avenues.

The CRMPs are a family of cytosolic phosphoproteins with five vertebrate family members (CRMP1-5) (Goshima et al., 1995; Minturn et al., 1995; Byk et al., 1996; Gaetano et al., 1997; Inatome et al., 2000). CRMP1-4 alleles each produce two transcripts, a and b, and CRMPb variants are longer amino terminal variants of the originally identified CRMPa isoforms (Yuasa-Kawada et al., 2003). Although CRMPs share significant sequence similarity with dihydropyrimidinase (DHPase), an enzyme involved in pyrimidine catabolism, no DHPase activity has been described for CRMPs (Wang and Strittmatter, 1997). Rather, a role for CRMPs in axon growth and pathfinding has been revealed. CRMPs are homologs of UNC-33, a protein that influences axon guidance and extension in *C. elegans* (Hedgecock et al., 1985; Siddiqui and Culotti, 1991). CRMP2 mediates growth cone collapse in response to the repulsive guidance cue Semaphorin3A (Goshima et al., 1995), and CRMP2 and CRMP4 influence neurite outgrowth (Minturn et al., 1995; Quinn et al., 1999; Quinn et al., 2003; Yoshimura et al., 2005).

Mechanistically, CRMP2 can bind to tubulin heterodimers and organizes microtubule assembly to establish axon-dendrite fate during development (Fukata et al., 2002b; Arimura et al., 2005) and CRMP4 can promote F-actin bundling (Rosslenbroich et al., 2005). Further, a role for CRMP2 in endocytosis has been described (Nishimura et al., 2003) and an association between CRMP4b and intersectin, an endocytic-exocytic adaptor protein, is consistent with an endocytic role for this isoform (Quinn et al., 2003).

The role of the CRMP proteins in nervous system injury and regeneration has not been extensively studied; however CRMP2a does have a potent neurite elongating effect in nerve regeneration in vivo (Suzuki et al., 2003). CRMP1a, CRMP2a and CRMP5a mRNA levels increase after hypoglossal nerve injury and CRMP4a expression is increased in regenerating adult sciatic motor neurons (Minturn et al., 1995; Suzuki et al., 2003) suggesting a more general role for CRMP proteins in the neuronal response to injury.

SUMMARY OF THE INVENTION

In accordance with an embodiment of the present invention, there is provided a novel method to promote regeneration of neurons after injury to the CNS or PNS. More specifically, this method comprises the use (or administration) of an antagonist to CRMP4-RhoA interaction in order to circumvent myelin-dependent inhibition of neuron regeneration. C4RIP has been identified as an antagonist of this type.

The surprising finding that CRMP4b interacts with RhoA in a Nogo-dependent manner led to the investigation of the potential role of this complex in the inhibition of neuron regeneration. This in turn resulted in the subsequent determination that antagonism of CRMP4 or of the CRMP4b-RhoA interaction attenuates neuron regeneration inhibition. This protein-protein interaction represents a novel, specific target for therapeutic intervention following CNS or PNS injury.

One of the advantages of the method of the present invention resides in the fact that the antagonist can be applied directly at the site of injury (i.e., in situ) in order to promote the regeneration of neurons.

The present invention further includes methods to identify compounds that disrupt CRMP4-RhoA interaction and that may thus be used to promote the regeneration of neurons.

In a screen to identify molecules that functionally interact with RhoA to mediate neuron regeneration inhibition, collapsin-response mediator protein 4b (CRMP4b) was identified as a molecule that interacts with Rho GTPase in a Nogo-dependent manner.

Other objects, advantages and features of the present invention will become more apparent upon reading of the following non restrictive description of preferred embodiments thereof, given by way of example only with reference to the accompanying drawings.

BRIEF DESCRIPTION OF THE DRAWINGS

FIG. 9: Rat CRMP4b amino acid and cDNA Sequence Date. (a) Rat CRMP4b amino acid sequence with C4RIP shaded in grey (SEQ ID NO: 1); (b) Rat C4RIP amino acid sequence (SEQ ID NO: 2); (c) Rat CRMP4b cDNA sequence with C4RIP shaded in grey (SEQ ID NO: 3); (d) Rat C4RIP cDNA sequence (SEQ ID NO: 4); (e) Rat CRMP4a amino acid sequence (SEQ ID NO: 5); and (f) Rat CRMP4a cDNA nucleotide sequence (SEQ ID NO: 6).

FIG. 10: Examples of membrane-translocating sequences that may be suitable for therapeutic applications involving C4RIP or derivatives, analogs, variants or fragments of C4RIP. (a) C4RIP sequence with C3-05 internalizing sequence (SEQ ID NOS: 8 and 9); (b) C3-05 MTS (SEQ ID NO: 10); (c) C4RIP sequence with Kaposi MTS (SEQ ID NOS: 11 and 12); and (d) Kaposi MTS

Figure 1:
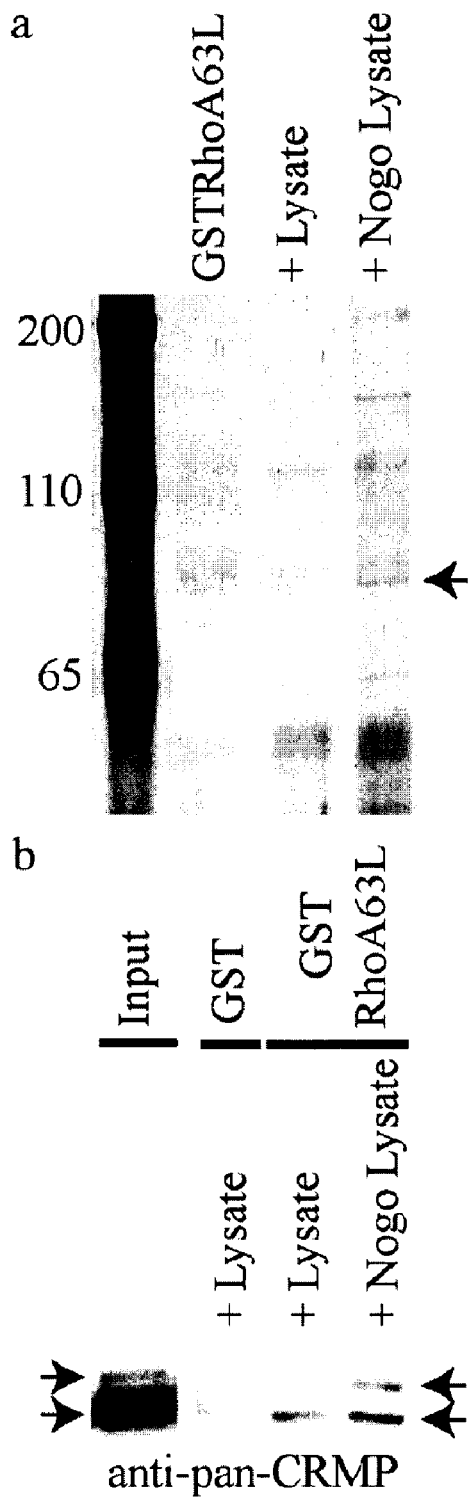
FIG. 1: A novel RhoA-CRMP4 interaction is enhanced by Nogo-66. (a) GSTRhoA63L pull down from PC12 cells stimulated with AP (+lysate) or AP-Nogo-66 (+Nogo lysate). Precipitation of a 75 kDa protein identified as CRMP4b by tandem mass spectrometry is enhanced in the AP-Nogo-66-stimulated lysate (arrow). The protein runs slightly below a non-specific protein from the GSTRhoA63L purification, which is visible in all lanes. The GSTRhoA63L lane represents beads that were not incubated with lysates. (b) GST and GSTRhoA63L pull downs from PC12 cell lysates immunoblotted with a pan-CRMP antibody. CRMPa (65 kDa) and CRMPb (75 kDa) bands are indicated in the PC 2 input and pull down lanes (arrows).

DESCRIPTION OF THE PREFERRED
EMBODIMENTS

Definitions

Unless defined otherwise, all technical and scientific terms used herein have the same meanings as commonly understood by one of ordinary skill in the art to which this invention belongs. Although methods and materials similar or equivalent to those described herein can be used in the practice or testing of the present invention, the preferred methods, devices, and materials are now described. All publications mentioned herein are incorporated by reference for the purpose of describing and disclosing the cell lines, vectors, and methodologies which are reported in the publications and which might be used in connection with the invention. The terminology used herein is for the purpose of describing particular embodiments only and is not intended to limit the scope of the present invention.

Use of the singular forms "a," "an," and "the" include plural references unless the context clearly dictates otherwise. Thus, for example, reference to "a target polynucleotide" includes a plurality of target polynucleotides.

As used in this specification and claim(s), the words "comprising" (and any form of comprising, such as "comprise" and "comprises"), "having" (and any form of having, such as "have" and "has"), "including" (and any form of including, such as "include" and "includes") or "containing" (and any form of containing, such as "contain" and "contains"), are inclusive or open-ended and do not exclude additional, unrecited elements or process steps.

The term "about" is used to indicate that a value includes an inherent variation of error for the device or the method being employed to determine the value.

The term "CRMP4", as used herein, is intended to include the native CRMP4 peptide as well as any biologically active fragment(s) or analog(s) thereof, including but not limited to CRMP4a and CRMP4b. The terms "fragment" and "analog" are used interchangeably herein to describe CRMP4 peptides useful in the methods of the present invention, as described more particularly in the Detailed Description.

The term "CRMP4" also encompasses variants and functional analogs of CRMP4 having a homologous amino acid sequence with a CRMP4 peptide. The present invention thus includes pharmaceutical formulations comprising such CRMP4 variants and functional analogs, carrying modifications like substitutions, deletions, insertions, inversions or cyclisations, but nevertheless having substantially the biological activity as CRMP4. The term C4RIP means, in the context of the present invention, CRMP4b-RhoA Inhibitory Peptide, a peptide that represents the first 126 residues within the unique amino terminal domain of CRMP4b. (See FIG. 9.) The term "C4RIP", as used herein, is intended to include the native C4RIP peptide as well as any biologically active fragment(s) or analog(s) thereof.

The terms "fragment" and "analog" are used interchangeably herein to describe C4RIP peptides useful in the methods of the present invention. The present invention thus includes pharmaceutical formulations comprising such C4RIP variants and functional analogs, carrying modifications like substitutions, deletions, insertions, inversions or cyclisations, but nevertheless having substantially the biological activity as C4RIP.

The term "analog" refers to a peptide that is related to CRMP4 but which has been modified. This modification does not, however, alter the biological activity of the interaction domain. Reasons for modifications include, but are not limited to, increasing the peptide's stability and solubility, decreasing the probability of denaturation, modifying its ability to be post-translationally modified, reducing manufacturing costs and enhancing large-scale manufacturing.

The term "RhoA", as used herein, is intended to include the native RhoA peptide as well as any biologically active fragment(s) or analog(s) thereof. The terms "fragment" and "analog" are used interchangeably herein to describe RhoA peptides useful in the methods of the present invention.

The term "RhoA" also encompasses variants and functional analogs of RhoA having a homologous amino acid sequence with a RhoA peptide. The present invention thus includes pharmaceutical formulations comprising such RhoA variants and functional analogs, carrying modifications like substitutions, deletions, insertions, inversions or cyclisations, but nevertheless having substantially the biological activity as RhoA.

The term "antagonist" refers, in the context of the present invention, to a molecule that inhibits the biological activity normally associated with CRMP4-RhoA complex formation or interaction or that inhibits CRMP4 function. Examples of antagonists include, but are not limited to, C4RIP, C4RIP analogs and C4RIP derivatives.

The term "siRNA" means, in the context of the present application, small interfering RNA. Gene silencing or knockdown can be achieved through the use of synthetic, small interfering RNA.

The term "derivative" denotes, in the context of a functional derivative of a sequence whether a nucleic acid or amino acid sequence, a molecule that retains a biological activity (either function or structural) that is substantially similar to that of the original sequence. This functional derivative or equivalent may be a natural derivative or may be prepared synthetically. Such derivatives include amino acid sequences having substitutions, deletions, or additions of one or more amino acids, as well as chemical mimics, provided that the biological activity of the protein is conserved. The same applies to derivatives of nucleic acid sequences that can have substitutions, deletions, or additions of one or more nucleotides, provided that the biological activity of the sequence is generally maintained. When relating to a protein sequence, the substituting amino acid generally has chemicophysical properties that are similar to that of the substituted amino acid. The similar physicochemical properties include, similarities in charge, bulkiness, hydrophobicity, hydrophilicity and the like. The term derivative is intended to include fragments, segments, variants, analogs or chemical derivatives, including non-peptide chemical derivatives, of the subject matter of the present invention.

For purposes of the present invention, the terms "neurite outgrowth" and "neuron regeneration" are used synonymously.

The term "variant" as used herein is a polynucleotide or polypeptide that differs from a reference polynucleotide or polypeptide, respectively. A typical variant of a polynucleotide differs in nucleotide sequence from another reference polynucleotide. Differences in the nucleotide sequence of the variant may or may not alter the amino acid sequence of a polypeptide encoded by the reference polynucleotide. Nucleotide changes may result in amino acid substitutions, additions, insertions, deletions, fusions, and truncations in the polypeptide encoded by the reference sequence, as discussed below. A typical variant of a polypeptide differs in amino acid sequence from another reference polypeptide. Generally, differences are such that the sequences of the reference polypeptide and the variant are closely similar overall and, in many regions, identical. A variant and reference polypeptide may differ in amino acid sequence by one or more substitutions, additions, insertion, deletions in any combination. A substituted or inserted amino acid residue may or may not be one encoded by the genetic code. A variant of a polynucleotide or polypeptide may be naturally occurring such as an allelic or pseudoallelic variant, including polymorphisms or mutations at one or more bases, or it may be a variant that is not known to occur naturally. Non-naturally occurring variants of polynucleotides and polypeptides may be made by mutagenesis techniques or by direct synthesis. The term "mutant" is encompassed by the above definition of non-natural variants.

"splice variants" as referred to hereinafter are variants, which result from the differential or alternative splicing and assembly of exons present in a given gene. Typically, the encoded proteins will display total identity in most regions, but lower identity in the specific region encoded by different exons.

A "deletion", as used herein, refers to a change in either amino acid or nucleotide sequence in which one or more amino acids or nucleotide residues, respectively, are absent, as compared to a reference polypeptide or polynucleotide.

An "insertion" or "addition", as used herein, refers to a change in an amino acid or nucleotide sequence resulting in the addition of one or more amino acid or nucleotide residues, respectively, as compared to a reference polypeptide or polynucleotide.

A "substitution", as used herein, refers to the replacement of one or more amino acids or nucleotides by different amino acids or nucleotides, respectively, as compared to a reference polypeptide or polynucleotide.

The term "derivative", as used herein, refers to the chemical modification of CRMP4 or C4RIP. Illustrative of such modifications would be replacement of hydrogen by an alkyl, acyl, or amino group. A derivative of CRMP4 or C4RIP could also be generated by expression in a recombinant system using an appropriately modified DNA construct. Derivatives may or may not retain some of all of the essential biological characteristics of the natural molecule.

The term "identity" as used herein refers to a measure of the extent of identical nucleotides or amino acids that two or more polynucleotide or amino acid sequences have in common. In general, the sequences are aligned so that the highest order match is obtained, referred to as the "alignment". Such optimal alignments make use of gaps, which are inserted to maximize the number of matches using local homology algorithms, such as the Smith-Waterman alignment. The terms "identity", or "similarity", or "homology", or "alignment" are well known to skilled artisans and methods to perform alignments and measure identity are widely described and taught in the literature: Dayhoff et al., Meth Enzymol 1983; 91: 524—Lipman D J and Pearson W R, Science 1985; 227: 1435—Altschul et al., J Mol Biol 1990; 215: 403. —Pearson W R, Genomics 1991; 11: 635. —Gribskov M and Devreux J, eds. (1992) Sequence Analysis Primer, WH Freeman & Cie, New-York. —Altschul et al., Nature Gen 1994; 6: 119. Furthermore, methods to perform alignments and to determine identity and similarity are codified in computer programs and software packages, some of which may also be web-based and accessible on the Internet. Preferred software includes but is not limited to BLAST (Basic Local Alignment Search Tools), including Blastn, Blastp, Blastx, tBlastn (Altschul et al., J Mol Biol 1990; 215: 403), FastA and TfastA (Pearson and Lipman, PNAS 1988; 85: 2444), Lasergene99 (DNASTAR, Madison Wis.), Omiga 2.0 or MacVector (Oxford Molecular Group, Cambridge, UK), Wisconsin Package (Genetic Computer Group (GCG), Madison, Wis.), Vector NTI Suite (InforMax Inc., N. Bethesda, Md.), GeneJockey II (Biosoft, Cambridge, UK).

As an illustration, by a polynucleotide having a nucleotide sequence with at least, for example, 95% "identity" to a reference nucleotide sequence of SEQ ID NO:3, SEQ ID NO:4 or SEQ ID NO:6, it is intended that the nucleotide sequence of the polynucleotide is identical to the reference sequence except that the polynucleotide sequence may include up to five point mutations, or divergent nucleotides, per 100 nucleotides of the reference nucleotide sequence of SEQ ID NO:3, SEQ ID NO:4 or SEQ ID NO:6. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence.

These mutations of the reference sequence may occur at the 5' or 3' terminal positions of the reference nucleotide sequence or anywhere between those terminal positions, interspersed either individually among nucleotides in the reference sequence or in one or more continuous groups within the reference sequence.

Similarly, by a polypeptide having an amino acid sequence having at least, for example, 95% "identity" to a reference amino acid sequence of SEQ ID NO:1, SEQ ID NO:2 or SEQ ID NO:5, it is intended that the amino acid sequence of the polypeptide is identical to the reference sequence except that the polypeptide sequence may include up to five amino acid alterations for every 100 amino acids of the reference amino acid sequence of SEQ ID NO:1, SEQ ID NO:2 or SEQ ID NO:5. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence, or anywhere between those terminal positions, interspersed either individually among residues in the reference sequence or in one or more continuous groups within the reference sequence.

The term "biologically active" or "biological activity", as used herein, refer to a protein having structural, regulatory, biochemical, electrophysiological or cellular functions of a naturally occurring molecule. Likewise, "immunologically active" refers to the capability of the natural, recombinant, or synthetic CRMP4, C4RIP or RhoA, or any oligopeptide thereof, to induce a specific immune response in appropriate animals or cells and to bind with specific antibodies.

The term "modulate", as used herein, refers to a change or an alteration in the biological activity of CRMP4 or C4RIP. Modulation may be an increase or a decrease in protein activity, a change in binding characteristics, or any other change in the biological, functional or immunological properties of CRMP4 or C4RIP.

The term "portion", as used herein, with regard to a protein (as in "a portion of a given protein") refers to fragments of that protein. The fragments may range in size from four amino acid residues to the entire amino acid sequence minus one amino acid. Thus, a protein "comprising at least a portion of the amino acid sequence of SEQ ID NO:1, SEQ ID NO:2 or SEQ ID: NO:5" encompasses the full-length CRMP4, C4RIP or fragments thereof.

In another embodiment of the invention, polynucleotide sequences or fragments thereof which encode CRMP4 or C4RIP, or fusion proteins or functional equivalents thereof, may be used in recombinant DNA molecules to direct expression of CRMP4 or C4RIP. Due to the inherent degeneracy of the genetic code, other DNA sequences that encode substantially the same or a functionally equivalent amino acid sequence may be produced and these sequences may be used to clone and express CRMP4 or C4RIP.

In another embodiment of the invention, a natural, modified, or recombinant polynucleotide encoding CRMP4 or C4RIP may be ligated to a heterologous sequence to encode a fusion protein. For example, to screen peptide libraries for inhibitors of CRMP4-RhoA interaction, it may be useful to encode a chimeric CRMP4 or C4RIP protein that can be recognized by a commercially available antibody. A fusion protein may also be engineered to contain a cleavage site located between a CRMP4 or C4RIP encoding sequence and the heterologous protein sequence, so that CRMP4 or C4RIP may be cleaved and purified away from the heterologous moiety.

In another embodiment, the coding sequence of CRMP4 or C4RIP may be synthesized, in whole or in part, using chemical methods well known in the art (see Caruthers et al., Nuc. Acids Res. Symp. Ser. 1980; 215-23; Horn et al., Nuc. Acids Res. Symp. Ser. 1980; 225-232). Alternatively, the protein itself may be produced using chemical methods to synthesize the amino acid sequence of CRMP4 or C4RIP, or portions thereof. For example, peptide synthesis can be performed using various solid-phase techniques (Roberge et al., Science 1995; 269: 202) and automated synthesis may be achieved, for example, using the ABI 431A Peptide Synthesizer (Perkin Elmer).

The newly synthesized peptide may be substantially purified by preparative high performance liquid chromatography e.g., Creighton T. (1983) "Proteins, Structures and Molecular Principles", W. H. Freeman & Co., New York, N.Y.). The composition of the synthetic peptides may be confirmed by amino acid analysis or sequencing (e.g., the Edman degradation procedure; Creighton T (1983), supra). Additionally, the amino acid sequences of CRMP4 or C4RIP, or any parts thereof, may be altered during direct synthesis and/or combined using chemical methods with sequences from other proteins, or any part thereof, to produce a variant polypeptide.

In order to express a biologically active CRMP4 or C4RIP, the nucleotide sequence encoding CRMP4 or C4RIP or functional equivalents may be inserted into an appropriate expression vector, i.e., a vector, which contains the necessary elements for the transcription and translation of the inserted coding sequence.

Methods that are well known to those skilled in the art may be used to construct expression vectors containing a CRMP4 or C4RIP coding sequence and appropriate transcriptional and translational control elements. These methods include in vitro recombinant DNA techniques, synthetic techniques, and in vivo genetic recombination. Such techniques are described in "Molecular Cloning: A Laboratory Manual", Sambrook J, Ed., CSHL Press, 1989, Cold Spring Harbor, N.Y., and "Current Protocols in Molecular Biology", Ausubel et al., John Wiley & Sons, 1989, New York, N.Y.

A variety of expression vector/host systems may be utilized to contain and express a CRMP4 or C4RIP coding sequence. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus, CaMV; tobacco mosaic virus, TMV) or with bacterial expression vectors (e.g., Ti or pBR322 plasmids); or animal cell systems.

The "control elements" or "regulatory sequences" are those non-translated regions of the vector—enhancers, promoters, 5' and 3' untranslated regions—which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters such as the hybrid lacZ promoter of the Bluescript® phagemid (Stratagene, La Jolla, Calif.) or pSport1™ plasmid (Gibco BRL) and ptrp-lac hybrids, and the like may be used. Other preferred prokaryotic vectors include but are not limited to pQE-9, pQE60, pQE70 (Quiagen), pNH8A, pNH16a, pNH18a, pNH46A (Stratagene) ptrc99a, pKK223-3, pKK233-3, pDR540, pRIT5 (Pharmacia). The baculovirus polyhedrin promoter may be used in insect cells. Promoters or enhancers derived from the genomes of plant cells (e.g., heat shock, RUBISCO; and storage protein genes) or from plant viruses (e.g., viral promoters or leader sequences) may be cloned into the vector. In mammalian cell systems, promoters from mammalian genes or from mammalian viruses are preferable. If it is necessary to generate a cell line that contains multiple copies of the sequence encoding CRMP4 or C4RIP, vectors based on SV40 or EBV may be used with an appropriate selectable marker.

In bacterial systems, a number of expression vectors may be selected depending upon the use intended for CRMP4 or C4RIP. For example, when large quantities of CRMP4 or C4RIP are needed for the induction of antibodies, vectors, which direct high-level expression of fusion proteins that are readily purified, may be used. Such vectors include, but are not limited to, the multifunctional E. coli cloning and expression vectors such as Bluescript® (Stratagene, La Jolla, Calif.), in which the sequence encoding CRMP4 or C4RIP may be ligated into the vector in frame with sequences for the amino-terminal Methionine and the subsequent 7 residues of .beta.-galactosidase so that a hybrid protein is produced; pIN vectors (Van Heeke and Schuster, J. Biol. Chem. 1989; 264: 5503); and the like; pGEX vectors (Promega, Madison, Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems may be designed to include heparin, thrombin, or factor XA protease cleavage sites so that the cloned polypeptide of interest can be released from the GST moiety at will.

In addition to bacteria, eukaryotic microbes, such as yeast, may also be used as hosts. Laboratory strains of Saccharomyces cerevisiae, Baker's yeast, are most often used although a number of other strains or species are commonly available. Vectors employing, for example, the 2 .mu. origin of replication of Broach et al. (Meth Enzymol 1983; 101: 307), or other yeast compatible origins of replication (see, for example, Stinchcomb et al. Nature 1979: 282; 39, Tschumper et al., Gene 1980: 10; 157, Clarke et al., Meth Enzymol 1983; 101: 300) may be used. Control sequences for yeast vectors include promoters for the synthesis of glycolytic enzymes (Hess et al. J Adv Enzyme Reg 1968; 7: 149; Holland et al., Biochemistry 1978; 17: 4900). Additional promoters known in the art include the promoter for 3-phosphoglycerate kinase (Hitzeman et al., J Biol Chem 1980; 255: 2073), alcohol oxidase, and PGH. Other promoters, which have the additional advantage of transcription controlled by growth conditions and/or genetic background are the promoter regions for alcohol dehydrogenase 2, isocytochrome C, acid phosphatase, degradative enzymes associated with nitrogen metabolism, the alpha-factor system and enzymes responsible for maltose and galactose utilization. It is also believed that terminator sequences are desirable at the 3' end of the coding sequences. Such terminators are found in the 3' untranslated region following the coding sequences in yeast-derived genes. For reviews, see "Current Protocols in Molecular Biology", Ausubel et al., John Wiley & Sons, 1989, New York, N.Y. and Grant et al., Meth Enzymol. 1987; 153: 516.

In cases where plant expression vectors are used, the expression of a sequence encoding CRMP4 or C4RIP may be driven by any of a number of promoters. For example, viral promoters such as the 35S and 19S promoters of CaMV may be used alone or in combination with the omega leader sequence from TMV (Takamatsu et al., EMBO J. 1987; 6: 307; Brisson et al., Nature 1984; 310: 511). Alternatively, plant promoters such as the small subunit of RUBISCO or heat shock promoters may be used (Coruzzi et al., EMBO J 1984; 3: 1671; Broglie et al., Science 1984; 224: 838; Winter et al., Results Probl. Cell Differ 1991; 17: 85). These constructs can be introduced into plant cells by direct DNA transformation or pathogen-mediated transfection. Such techniques are described in a number of generally available reviews (see, for example, Hobbs S or Murry L E in "McGraw Hill Yearbook of Science and Technology" McGraw Hill, 1992, New York, N.Y.; pp. 191-196 or Weissbach and Weissbach in "Methods for Plant Molecular Biology", Academic Press, 1988, New York, N.Y.; pp. 421-463).

An insect system may also be used to express CRMP4 or C4RIP. For example, in one such system, *Autographa californica* nuclear polyhedrosis virus (AcNPV) is used as a vector to express foreign genes in *Spodoptera frugiperda* cells or in *Trichoplusia larvae*. The sequences encoding CRMP4 or C4RIP may be cloned into a nonessential region of the virus, such as the polyhedrin gene, and placed under control of the polyhedrin promoter. Successful insertion of CRMP4 or C4RIP will render the polyhedrin gene inactive and produce recombinant virus lacking coat protein. The recombinant viruses may then be used to infect, for example, *S. frugiperda* cells or *Trichoplusia larvae* in which CRMP4 or C4RIP may be expressed (Smith et al., J Virol 1983; 46: 584; Engelhard et al., Proc Natl Acad Sci 1994; 91: 3224).

In mammalian host cells, a number of viral-based expression systems may be utilized. In cases where an adenovirus is used as an expression vector, a sequence encoding CRMP4 or C4RIP may be ligated into an adenovirus transcription/translation complex consisting of the late promoter and tripartite leader sequence. Insertion in a non-essential E1 or E3 region of the viral genome may be used to obtain a viable virus, which is capable of expressing CRMP4 or C4RIP in infected host cells (Logan and Shenk, Proc Natl Acad Sci 1984; 81: 3655). In addition, transcription enhancers, such as the Rous sarcoma virus (RSV) enhancer, may be used to increase expression in mammalian host cells.

Specific initiation signals may also be used to achieve more efficient translation of a sequence encoding CRMP4 or C4RIP. Such signals include the ATG initiation codon and adjacent sequences. In cases where sequences encoding CRMP4 or C4RIP, their initiation codons and upstream sequences are inserted into the appropriate expression vector, no additional transcriptional or translational control signals may be needed. However, in cases where only coding sequence, or a portion thereof, is inserted, exogenous translational control signals including the ATG initiation codon should be provided. Furthermore, the initiation codon should be in the correct reading frame to ensure the correct translation of the entire insert. Exogenous translational elements and initiation codons may be of various origins, both natural and synthetic. The efficiency of expression may be enhanced by the inclusion of enhancers which are appropriate for the particular cell system which is used, such as those described in the literature (Scharf et al., Results Probl Cell Differ 1994; 20: 125; Bittner et al., Meth Enzymol 1987; 153: 516).

In addition, a host cell strain may be chosen for its ability to modulate the expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to facilitate correct insertion, folding and/or function. Different host cells such as CHO, HeLa, MDCK, HEK293, WI38, and COS, which have specific cellular machinery and characteristic mechanisms for such post-translational activities, may be chosen to ensure the correct modification and processing of the foreign protein.

For long-term, high-yield production of recombinant proteins, stable expression is preferred. For example, cell lines, which stably express CRMP4 or C4RIP, may be transformed using expression vectors which may contain viral origins of replication and/or endogenous expression elements and a selectable marker gene on the same or separate vector. Following the introduction of the vector, cells may be allowed to grow for 1-2 days in an enriched media before they are switched to selective media. The purpose of the selectable marker is to confer resistance to selection, and its presence allows growth and recovery of cells, which successfully express the introduced sequences. Resistant clones of stably transformed cells may be proliferated using tissue culture techniques appropriate to the cell type.

Any number of selection systems may be used to recover transformed cell lines. These include, but are not limited to, the herpes simplex virus thymidine kinase (Wigler et al., Cell 1977; 11: 223) and adenine phospho-ribosyltransferase (Lowy et al., Cell 1980; 22: 817) genes which can be employed in tk.+−. or aprt.+−.cells, respectively. Also, antimetabolite, antibiotic, or herbicide resistance can be used as the basis for selection; for example, dhfr, which confers resistance to methotrexate (Wigler et al., Proc Natl Acad Sci 1980; 77: 3567); npt, which confers resistance to the aminoglycosides neomycin and G418 (Colbere-Garapin et al., J Mol Biol 1981; 150: 1) and als or pat, which confer resistance to chlorsulfuron and phosphinotricin acetyltransferase, respectively (Murry L E, supra). Additional selectable genes have been described, for example, trpB, which allows cells to utilize indole in place of tryptophan, or hisD, which allows cells to utilize histinol in place of histidine (Hartman and Mulligan, Proc Natl Acad Sci 1988; 85: 8047). Recently, the use of visible markers has gained popularity with such markers as anthocyanins, .beta.-glucuronidase and its substrate GUS, and luciferase and its substrate luciferin, being widely used not only to identify transformants, but also to quantify the amount of transient or stable protein expression attributable to a specific vector system (Rhodes et al., Methods Mol Biol 1995; 55: 121).

Although the presence/absence of marker gene expression suggests that the gene of interest is also present, its presence and expression may need to be confirmed. For example, if the sequence encoding CRMP4 or C4RIP is inserted within a marker gene sequence, recombinant cells containing sequences encoding CRMP4 or C4RIP can be identified by the absence of marker gene function. Alternatively, a marker gene can be placed in tandem with a sequence encoding CRMP4 or C4RIP under the control of a single promoter. Expression of the marker gene in response to induction or selection usually indicates expression of the tandem gene as well.

Alternatively, host cells that contain the coding sequence for CRMP4 or C4RIP and that express CRMP4 or C4RIP may be identified by a variety of procedures known to those of skill in the art. These procedures include, but are not limited to, DNA-DNA or DNA-RNA hybridizations and protein bioassay or immunoassay techniques, which include membrane, solution, or chip-based technologies for the detection and/or quantification of the nucleic acid or protein.

The presence of the polynucleotide sequence encoding CRMP4 or C4RIP can be detected by DNA-DNA or DNA-RNA hybridization or amplification using probes or portions or fragments of polynucleotides encoding CRMP4 or C4RIP. Nucleic acid amplification based assays involve the use of oligonucleotides or oligomers based on the CRMP4- and C4RIP-encoding sequences to detect transformants containing DNA or RNA encoding CRMP4 and C4RIP. As used herein "oligonucleotides" or "oligomers" refer to a nucleic acid sequence of at least about 10 nucleotides and as many as about 60 nucleotides, preferably about 15 to 30 nucleotides, and more preferably about 20-25 nucleotides, which can be used as a probe.

A variety of protocols for detecting and measuring the expression of CRMP4 or C4RIP, using either polyclonal or monoclonal antibodies specific for the protein are known in the art. Examples include enzyme-linked immunosorbent assay (ELISA), radioimmunoassay (RIA), and fluorescent activated cell sorting (FACS). A two-site, monoclonal-based immunoassay utilizing monoclonal antibodies reactive to two non-interfering epitopes on CRMP4 or C4RIP may be preferred, but a competitive binding assay may be employed. These and other assays are described, among other places, in "Serological Methods: A Laboratory Manual", Hampton et al., APS Press, 1990, St-Paul, Mich. and Maddox et al., J Exp Med 1983; 158: 1211).

A wide variety of labels and conjugation techniques are known by those skilled in the art and may be used in various nucleic acid and amino acid assays. Means for producing labeled hybridization or PCR probes for detecting sequences related to polynucleotides encoding CRMP4 or C4RIP include oligolabeling, nick translation, end-labeling or PCR amplification using a labeled nucleotide. Alternatively, the sequence encoding CRMP4 or C4RIP, or any portion of it, may be cloned into a vector for the production of an mRNA probe. Such vectors are known in the art, are commercially available, and may be used to synthesize RNA probes in vitro by addition of an appropriate RNA polymerase such as T7, T3 or SP6 and labeled nucleotides. These procedures may be conducted using a variety of commercially available kits: from e.g. Pharmacia & Upjohn, (Kalamazoo, Mich.); Promega (Madison Wis.); and U.S. Biochemical Corp. (Cleveland, Ohio), or Ambion (Austin, Tex.). Suitable reporter molecules or labels, which may be used, include radionuclides, enzymes, fluorescent, chemiluminescent, or chromogenic agents as well as substrates, cofactors, inhibitors, magnetic particles, and the like.

Host cells transformed with a nucleotide sequence encoding CRMP4 or C4RIP may be cultured under conditions suitable for the expression and recovery of the protein from cell culture. The protein produced by a recombinant cell may be secreted or contained intracellularly depending on the sequence and/or the vector used. As will be understood by those of skill in the art, expression vectors containing polynucleotides, which encode CRMP4 or C4RIP may be designed to contain signal sequences that direct secretion of CRMP4 or C4RIP through a prokaryotic or eukaryotic cell membrane. Other recombinant constructions may be used to join sequences encoding CRMP4 or C4RIP to a nucleotide sequence encoding a polypeptide domain, which will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp., Seattle, Wash.).

In addition to recombinant production, fragments of CRMP4 or C4RIP may be produced by direct peptide synthesis using solid-phase techniques (see Stewart et al., "Solid-Phase Peptide Synthesis", WH Freeman & Co., 1969, San Francisco, Calif.; Merrifield et al., J Am Chem Soc 1963; 85: 2149). Chemical synthesis may be performed using manual techniques or by automation. Automated synthesis may be achieved, for example, using Applied Biosystems 431A Peptide Synthesizer (Perkin Elmer). Various fragments of CRMP4 or C4RIP may be chemically synthesized separately and combined using chemical methods to produce the full-length molecule.

In other embodiments of the invention, CRMP4 or C4RIP or fragments thereof may be used for therapeutic, diagnostic or screening purposes.

Antibodies may be generated using methods that are well known in the art. Such antibodies may include, but are not limited to, polyclonal, monoclonal, chimeric, single chain, Fab fragments, and fragments produced by a Fab expression library. Neutralizing antibodies, (i.e., those which inhibit dimer formation) are especially preferred for therapeutic use.

For the production of antibodies, various hosts including goats, rabbits, rats, mice, humans, and others, may be immunized by injection with CRMP4 or C4RIP or any fragment or oligopeptide thereof which has immunogenic properties. Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, keyhole limpet hemocyanin, and dinitrophenol. Among adjuvants used in humans, BCG (bacilli Calmette-Guerin) and *Corynebacterium parvum* are especially preferable.

It is preferred that the peptides, fragments, or oligopeptides used to induce antibodies to CRMP4 or C4RIP have an amino acid sequence consisting of at least five amino acids, and more preferably at least 10 amino acids. It is also preferable that they are identical to a portion of the amino acid sequence of the natural protein, and they may contain the entire amino acid sequence of a small, naturally occurring molecule. Short stretches of CRMP4 or C4RIP amino acids may be fused with those of another protein such as keyhole limpet hemocyanin and antibody produced against the chimeric molecule.

Various immunoassays may be used for screening to identify antibodies having the desired specificity. Numerous protocols for competitive binding or immunoradiometric assays using either polyclonal or monoclonal antibodies with established specificities are well known in the art. Such immunoassays typically involve the measurement of complex formation between CRMP4 or C4RIP and its specific antibody. A two-site, monoclonal-based immunoassay utilizing monoclonal antibodies reactive to two non-interfering CRMP4 or C4RIP epitopes may be preferred, but a competitive binding assay may also be employed (Maddox, supra).

In another embodiment of the invention, the polynucleotides encoding CRMP4, C4RIP, or any fragment thereof, or antisense or siRNA sequences, may be used for therapeutic purposes. In one aspect, antisense or siRNA to the polynucleotide encoding CRMP4 or C4RIP may be used in situations in which it would be desirable to block the synthesis of the protein. In particular, cells may be transformed with sequences complementary to polynucleotides encoding CRMP4 or C4RIP. Thus, antisense or siRNA sequences may be used to modulate CRMP4 or C4RIP activity, or to achieve regulation of gene function. Such technology is now well known in the art, and siRNA, sense or antisense oligomers or larger fragments, can be designed from various locations along the coding or control regions of sequences encoding CRMP4 or C4RIP.

Still in the realm of therapeutics, C4RIP or derivatives, analogs, variants or fragments of C4RIP, may be engineered to include an inherent cell membrane-translocating sequence (or MTS). The inclusion of such a MTS, also called an "internalization" or "internalizing" sequence, allows a translated peptide to be transported across a cell membrane (Rojas et al. 1998; Winton et al. 2002). This opens up the possibility of therapeutic applications in living systems. Two example MTSs are illustrated with and without C4RIP in FIG. 10. FIG. 10 a) shows the C4RIP sequence with the C3-05 internalizing sequence, while FIG. 10 c) illustrates the C4RIP sequence with the Kaposi MTS. FIG. 10 b) and d) show the C3-05 MTS and Kaposi MTS, respectively. It is expected that other internalizing sequences would function with C4RIP, and therefore the scope of the present invention is meant to encompass any MTS that would have the desired effect of transporting C4RIP or derivatives, analogs, variants or fragments of C4RIP across a cell membrane.

Expression vectors derived from retroviruses, adenovirus, herpes or vaccinia viruses, or from various bacterial plasmids may be used for delivery of nucleotide sequences to the targeted organ, tissue or cell population. Methods, which are well known to those skilled in the art, can be used to construct recombinant vectors which will express antisense polynucleotides of the gene encoding CRMP4 or C4RIP. These techniques are described both in Sambrook et al. (supra) and in Ausubel et al. (supra).

Transient expression may last for a month or more with a non-replicating vector and even longer if appropriate replication elements are part of the vector system.

As mentioned above, modifications of gene expression can be obtained by designing antisense molecules, DNA, RNA or PNA, to the control regions of the gene encoding CRMP4 i.e., the promoters, enhancers, and introns. Oligonucleotides derived from the transcription initiation site, e.g., between positions −10 and +10 from the 5' end of the transcript, are preferred. Similarly, inhibition can be achieved using "triple helix" base-pairing methodology. Triple helix pairing is useful because it causes inhibition of the ability of the double helix to open sufficiently for the binding of polymerases, transcription factors, or regulatory molecules. Recent therapeutic advances using triplex DNA have been described in the literature (Gee, J. E. et al. (1994) In: Huber, B. E. and Carr, B. I. Molecular and Immunologic Approaches, Futura Publishing Co., Mt. Kisco, N.Y.). The antisense molecules may also be designed to block translation of mRNA by preventing the transcript from binding to ribosomes.

Ribozymes, enzymatic RNA molecules, may also be used to catalyze the specific cleavage of RNA. The mechanism of ribozyme action involves sequence-specific hybridization of the ribozyme molecule to complementary target RNA, followed by endonucleolytic cleavage. Examples which may be used include engineered hammerhead motif ribozyme molecules that can specifically and efficiently catalyze endonucleolytic cleavage of sequences encoding CRMP4 or C4RIP.

Specific ribozyme cleavage sites within any potential RNA target are initially identified by scanning the target molecule for ribozyme cleavage sites which include the following sequences: GUA, GUU, and GUC. Once identified, short RNA sequences of between 15 and 20 ribonucleotides corresponding to the region of the target gene containing the cleavage site may be evaluated for secondary structural features which may render the oligonucleotide inoperable. The suitability of candidate targets may also be evaluated by testing accessibility to hybridization with complementary oligonucleotides using ribonuclease protection assays.

Antisense molecules and ribozymes of the invention may be prepared by any method known in the art for the synthesis of RNA molecules. These include techniques for chemically synthesizing oligonucleotides such as solid phase phosphoramidite chemical synthesis. Alternatively, RNA molecules may be generated by in vitro and in vivo transcription of DNA sequences encoding CRMP4 or C4RIP. Such DNA sequences may be incorporated into a wide variety of vectors with suitable RNA polymerase promoters such as T7 or SP6. Alternatively, these cDNA constructs that synthesize antisense RNA constitutively or inducibly can be introduced into cell lines, cells, or tissues.

RNA molecules may be modified to increase intracellular stability and half-life. Possible modifications include, but are not limited to, the addition of flanking sequences at the 5' and/or 3' ends of the molecule or the use of phosphorothioate or 2' O-methyl rather than phosphodiesterase linkages within the backbone of the molecule. This concept is inherent in the production of PNAs and can be extended in all of these molecules by the inclusion of nontraditional bases such as inosine, queosine, and wybutosine, as well as acetyl-, methyl-, thio-, and similarly modified forms of adenine, cytidine, guanine, thymine, and uridine which are not as easily recognized by endogenous endonucleases.

Many methods for introducing vectors into cells or tissues are available and equally suitable for use in vivo, in vitro, and ex vivo. For ex vivo therapy, vectors may be introduced into stem cells taken from the patient and clonally propagated for autologous transplant back into that same patient. Delivery by transfection and by liposome injections may be achieved using methods that are well known in the art.

Any of the therapeutic methods described above may be applied to any suitable subject including, for example, mammals such as dogs, cats, cows, horses, rabbits, monkeys, and most preferably, humans.

An additional embodiment of the invention relates to the administration of a pharmaceutical composition, in conjunction with a pharmaceutically acceptable carrier, for any of the therapeutic effects discussed above. Such pharmaceutical compositions may consist of CRMP4 or C4RIP, antibodies to CRMP4 or C4RIP, mimetics, agonists, antagonists, or inhibitors of CRMP4 or C4RIP. The compositions may be administered alone or in combination with at least one other agent, such as stabilizing compound, which may be administered in any sterile, biocompatible pharmaceutical carrier, including, but not limited to, saline, buffered saline, dextrose, and water. The compositions may be administered to a patient alone, or in combination with other agents, drugs or hormones.

The pharmaceutical compositions of the present invention may be manufactured in a manner that is known in the art, e.g., by means of conventional mixing, dissolving, granulating, dragee-making, levigating, emulsifying, encapsulating, entrapping, or lyophilizing processes.

The pharmaceutical composition may be provided as a salt and can be formed with many acids, including but not limited to, hydrochloric, sulfuric, acetic, lactic, tartaric, malic, succinic, etc. Salts tend to be more soluble in aqueous or other protonic solvents than are the corresponding free base forms. In other cases, the preferred preparation may be a lyophilized powder which may contain any or all of the following: 1-50 mM histidine, 0.1%-2% sucrose, and 2-7% mannitol, at a pH range of 4.5 to 5.5, that is combined with buffer prior to use.

After pharmaceutical compositions have been prepared, they can be placed in an appropriate container and labeled for treatment of an indicated condition. For administration of CRMP4 or C4RIP, such labeling would include amount, frequency, and method of administration. Pharmaceutical compositions suitable for use in the invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays, e.g., of neurite outgrowth, or in animal models, usually mice, rats or monkeys. The animal model may also be used to determine the appropriate concentration range and route of administration. Such information can then be used to determine useful doses and routes for administration in humans. A therapeutically effective dose refers to that amount of active ingredient, for example CRMP4 or C4RIP or fragments thereof, antibodies of CRMP4 or C4RIP, agonists, antagonists or inhibitors of CRMP4 or C4RIP, which ameliorates the symptoms or condition. Therapeutic efficacy and toxicity may be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between therapeutic and toxic effects is the therapeutic index, and it can be expressed as the ratio, $LD_{50}/ED_{50}$.

Pharmaceutical compositions, which exhibit large therapeutic indices are preferred. The data obtained from cell culture assays and animal studies is used in formulating a range of dosage for human use. The dosage contained in such compositions is preferably within a range of circulating concentrations that include the ED50 with little or no toxicity. The dosage varies within this range depending upon the dosage form employed, sensitivity of the patient, and the route of administration.

The exact dosage will be determined by the practitioner, in light of factors related to the subject that requires treatment. Dosage and administration are adjusted to provide sufficient levels of the active moiety or to maintain the desired effect. Factors, which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

Normal dosage amounts may vary from 0.1 to 100,000 micrograms, up to a total dose of about 1 g, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

In one aspect, hybridization with PCR probes which are capable of detecting polynucleotide sequences, including genomic sequences, encoding CRMP4 or C4RIP or closely related molecules, may be used to identify nucleic acid sequences which encode CRMP4 or C4RIP. The specificity of the probe, whether it is made from a highly specific region, e.g., 10 unique nucleotides in the 5' regulatory region, or a less specific region, e.g., especially in the 3' coding region, and the stringency of the hybridization or amplification (maximal, high, intermediate, or low) will determine whether the probe identifies only naturally occurring sequences encoding CRMP4 or C4RIP, alleles, or related sequences.

Probes may also be used for the detection of related sequences, and should preferably contain at least 50% of the nucleotides from any of the CRMP4 or C4RIP encoding sequences. The hybridization probes of the subject invention may be DNA or RNA and derived from the nucleotide sequence of SEQ ID NO:3, SEQ ID NO:4 or SEQ ID NO:6 or from genomic sequence including promoter, enhancer elements, and introns of the naturally occurring CRMP4 or C4RIP.

Means for producing specific hybridization probes for DNAs encoding CRMP4 or C4RIP include the cloning of nucleic acid sequences encoding CRMP4 or C4RIP or CRMP4 or C4RIP derivatives into vectors for the production of mRNA probes. Such vectors are known in the art, commercially available, and may be used to synthesize RNA probes in vitro by means of the addition of the appropriate RNA polymerases and the appropriate labeled nucleotides. Hybridization probes may be labeled by a variety of reporter groups, for example, radionuclides such as 32P or 35S, or enzymatic labels, such as alkaline phosphatase coupled to the probe via avidin/biotin coupling systems, and the like. Polynucleotide sequences encoding CRMP4 may be used for the diagnosis of conditions or diseases that are associated with expression of CRMP4. Examples of such conditions or diseases include, but may not be limited to, injuries or damage to the central and peripheral nervous systems. The polynucleotide sequences encoding CRMP4 or C4RIP may be used in Southern or northern analysis, dot blot, or other membrane-based technologies; in PCR technologies; or in dip stick, pin, ELISA or chip assays utilizing fluids or tissues from patient biopsies to detect altered CRMP4 or C4RIP expression. Such qualitative or quantitative methods are well known in the art.

In a particular aspect, the nucleotide sequences encoding CRMP4 may be useful in assays that detect activation or induction of various neurological or other non-neurological disorders, particularly those mentioned above. The nucleotide sequence encoding CRMP4 may be labeled by standard methods, and added to a fluid or tissue sample from a patient under conditions suitable for the formation of hybridization complexes. After a suitable incubation period, the sample is washed and the signal is quantitated and compared with a standard value. If the amount of signal in the biopsied or extracted sample is significantly altered from that of a comparable control sample, the nucleotide sequence has hybridized with nucleotide sequences in the sample, and the presence of altered levels of nucleotide sequences encoding CRMP4 in the sample indicates the presence of the associated disease. Such assays may also be used to evaluate the efficacy of a particular therapeutic treatment regimen in animal studies, in clinical trials, or in monitoring the treatment of an individual patient.

In order to provide a basis for the diagnosis of disease associated with expression of CRMP4, a normal or standard profile for expression is established. This may be accomplished by combining body fluids or cell extracts taken from normal subjects, either animal or human, with a sequence, or a fragment thereof, which encodes CRMP4, under conditions suitable for hybridization or amplification. Standard hybridization may be quantified by comparing the values obtained from normal subjects with those from an experiment where a known amount of a substantially purified polynucleotide is used. Standard values obtained from normal samples may be compared with values obtained from samples from patients who are symptomatic for disease. Deviation between standard and subject values is used to establish the presence of disease.

Once disease is established and a treatment protocol is initiated, hybridization assays may be repeated on a regular basis to evaluate whether the level of expression in the patient begins to approximate that which is observed in the normal patient. The results obtained from successive assays may be used to show the efficacy of treatment over a period ranging from several days to months.

With respect to neurological diseases, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the disease.

Additional diagnostic uses for oligonucleotides encoding CRMP4 may involve the use of PCR. Such oligomers may be chemically synthesized, generated enzymatically, or produced from a recombinant source. Oligomers will preferably consist of two nucleotide sequences, one with sense orientation and another with antisense, employed under optimized conditions for identification of a specific gene or condition. The same two oligomers, nested sets of oligomers, or even a degenerate pool of oligomers may be employed under less stringent conditions for detection and/or quantitation of closely related DNA or RNA sequences.

Methods which may also be used to quantitate the expression of CRMP4 or C4RIP include radiolabeling or biotinylating nucleotides, coamplification of a control nucleic acid, and standard curves onto which the experimental results are interpolated (Melby, P. C. et al. (1993) J. Immunol. Methods, 159:235-244; Duplaa, C. et al. (1993) Anal. Biochem. 229-236). The speed of quantitation of multiple samples may be accelerated by running the assay in an ELISA format where the oligomer of interest is presented in various dilutions and a spectrophotometric or colorimetric response gives rapid quantitation.

In another embodiment of the invention, the nucleic acid sequence that encodes CRMP4 may also be used to generate hybridization probes that are useful for mapping the naturally occurring genomic sequence. The sequence may be mapped to a particular chromosome or to a specific region of the chromosome using well-known techniques. Such techniques include FISH, FACS, or artificial chromosome constructions, such as yeast artificial chromosomes, bacterial artificial chromosomes, bacterial P1 constructions or single chromosome cDNA libraries as reviewed by Price, C. M. (1993; Blood Rev. 7:127-134), and Trask, B. J. (1991; Trends Genet. 7:149-154).

Screening Assays

In other embodiments of the invention, CRMP4 and C4RIP, their catalytic or immunogenic fragments, or oligopeptides thereof can be used for screening libraries of compounds in any of a variety of drug screening techniques. The fragment employed in such screening may be free in solution, affixed to a solid support, borne on a cell surface, or located intracellularly. The formation of binding complexes, between CRMP4 or C4RIP and the agent being tested, may be measured. Thus, the polypeptides of the invention may also be used to assess the binding of small molecule substrates and ligands in, for example, cells, cell-free preparations, chemical libraries, and natural product mixtures. These substrates and ligands may be natural substrates and ligands or may be structural or functional mimetics. In general, such screening procedures involve producing appropriate cells, which express the receptor polypeptides of the present invention on the surface thereof. Such cells include cells from mammals, yeast, insects (i.e., *Drosophila*) or bacteria (i.e., *E. coli*). Cells expressing the receptor (or cell membranes containing the expressed receptor) are then contacted with a test compound to observe binding, or stimulation or inhibition of a functional response (for example, interference with the CRMP4-RhoA interaction).

The assays may simply test binding of a candidate compound wherein adherence to the cells bearing the receptor is detected by means of a label directly or indirectly associated with the candidate compound or in an assay involving competition with a labeled competitor. Further, these assays may test whether the candidate compound results in a signal generated by activation of the receptor, using detection systems appropriate to the cells bearing the receptor at their surfaces (for example increased ion permeation measured by patch clamp or, preferably by ion imaging). Inhibitors of activation are generally assayed in the presence of a known agonist (for example, protons) and the effect of the candidate compound on the activation by the agonist is observed. Standard methods for conducting such screening assays are well understood in the art. Typically, the response may be measured by use of a microelectrode technique accompanied by such measurement strategies as voltage clamping of the cell whereby activation of ion channels may be identified by inward or outward current flow as detected using the microelectrodes. $^{22}$Na, $^{86}$Rb, $^{45}$Ca radiolabeled cations or $^{14}$C or $^{3}$H guanidine may be used to assess such ion flux; a sodium, calcium or potassium ion sensitive dye (such as Fura-2, or Indo) may also be used to monitor ion passage through the receptor ion channel, or a potential sensitive dye may be used to monitor potential changes, such as in depolarization.

Another technique for drug screening, which may be used provides for high throughput screening of compounds having suitable binding affinity to the protein of interest as described in published PCT application WO84/03564. In this method, as applied to CRMP4 or C4RIP large numbers of different small test compounds are synthesized on a solid substrate, such as plastic pins or some other surface. The test compounds are reacted with a CRMP4-RhoA conjugate and washed. Bound CRMP4-RhoA conjugate is then detected by methods well known in the art. Purified CRMP4 or C4RIP can also be coated directly onto plates for use in the aforementioned drug screening techniques. Alternatively, non-neutralizing antibodies can be used to capture the peptide and immobilize it on a solid support.

In another embodiment, one may use competitive drug screening assays in which neutralizing antibodies capable of binding to the CRMP4-RhoA conjugate specifically compete with a test compound for binding CRMP4 or C4RIP. In this manner, the antibodies can be used to detect the presence of any peptide that shares one or more antigenic determinants with CRMP4 or C4RIP.

The drug assays or screens described above, as well as any other that are known to the person of skill in the art and that may be suitable to practice the present invention, may be packaged in a kit. All kits of this type are intended to be included within the scope of the present invention.

While the present invention is described with particular reference to the CNS, it is believed that it will also find application in the PNS because other antagonists targeting intracellular signalling substrates that are convergent targets of MAIs and CSPGs have demonstrated efficacy in both CNS and PNS regeneration models (Madura et al. 2007; Hiraga et al. (2006); Dergham et al. 2002; Fournier et al. 2003).

Methods and Materials

Plasmid Construction

To construct CRMP-V5 expression vectors, cDNA was amplified by polymerase chain reaction (PCR) from rat pEGFP-CRMP constructs (provided by Dr. Peter McPherson, McGill University). The PCR product was ligated into the HindIII- and XhoI-sites of pcDNA 3.1 V5-His for CRMP1a, CRMP2a and CRMP3a and into HindIII- and EcoRI-site of pcDNA 3.1 V5-His for CRMP4a. The cDNA for CRMP4b was amplified from pcDNA 3.1CRMP4bV5-His TOPO (Quinn et al., 2003) and ligated into the HindIII- and EcoRI-site pcDNA 3.1 V5-His in frame with the V5-His tag. CRMP1b-V5 was constructed by amplifying the coding sequence by PCR from an EST clone (IMAGE: 5686818) and ligated into EcoRI- and XhoI-sites of pcDNA 3.1 V5-His.

pcDNA myc-wild type RhoA (wt) was obtained from UMR cDNA Resource Center. pRK5 myc-Rac1 (wt), pRK5 myc-Cdc42 (wt), pRK5 myc-RhoA63L, pRK5 myc-RhoAN19, pRK5 myc-RacQ61L, pRK5 myc-RacN17, pRK5 myc-Cdc42Q61L and pRK5 myc-Cdc42N17 constructs were provided by Dr. Nathalie Lamarche-Vane (McGill University). FLAG-RhoA63L was generated by subcloning RhoA63L into the BamHI- and EcoRI-sites of pcDNA3FLAG. pCAG-myc-mROCK II construct was provided by Dr. Shuh Narumiya (Kyoto University).

To generate C4RIP-V5, the unique amino terminal domain of CRMP4b (residues 1-126) was introduced into the BamHI- and EcoRI-sites of pcDNA 3.1V5-His. pHSVC4RIP was generated by subcloning C4RIP-V5 into the HindIII- and SalI-sites of pHSVPrPUC. pHSVCRMP4bGFP was generated by cloning CRMP4b into the HindIII- and EcoRI-sites of pEGFP N2 (Clonetech) and subsequently sub-cloning into the HindIII- and XbaI-sites of pHSVPrPUC. Chimeric CRMP4bNCRMP2-V5 was constructed by PCR by ligating residues 14-572 of CRMP2a into EcoRI- and XhoI-sites of C4RIP-V5. CRMP4ΔN consists of CRMP4a with the first 12 residues replaced by a single methionine. CRMP4ΔN was amplified by PCR and ligated into HindIII- and EcoRI-sites of pcDNA 3.1 V5-His.

Preparation of Herpes Simplex Viruses pHSVPrPUC plasmids were transfected into 2-2 Vero cells which were superinfected with 5 dl 1.2 HSV helper virus 1 day later. Recombinant virus was amplified through three passages and stored at −80° C. as described previously (Neve et al., 1997).

Preparation of Recombinant Proteins

Stimulations to examine inhibitory responses were performed with alkaline-phosphatase-conjugated Nogo-66 (AP-Nogo-66) purified from stably transfected 293 cells or Nogo-P4 peptide or myelin. AP-Nogo-66 or AP was purified by $Ni^{2+}$ affinity chromatography as previously described (Nakamura et al., 1998; Fournier et al., 2001). For all treatments AP-Nogo66-His (8 nM) or AP (8 nM) was preaggregated with 100 ng/ml anti-human AP (Niederost et al., 2002). Nogo-P4 (Alpha Diagnostics, San Antonio, Tex.) is a 25 aa inhibitory peptide sequence (residues 31-55 of Nogo-66) sufficient to mediate the inhibitory properties of Nogo-66, a potent inhibitory component of Nogo-A (GrandPre et al., 2000). Myelin extracts were prepared from bovine brain as described previously (Igarashi et al., 1993; Hsieh et al., 2006).

GST, GST-RhoAWT and GST-RhoA63L (construct provided by Dr. Keith Burridge, University of North Carolina, Chapel Hill) were expressed in *Escherichia coli* and purified on glutathione-Sepharose as previously described (Arthur et al., 2002; Wennerberg et al., 2002). For overlay assays, RhoA was cleaved from the GST moiety via thrombin cleavage. Aggrecan was purchased from Sigma Chemical Co. (Oakville, Ontario).

GST-RhoA Pull Down Assays

PC12 cells were grown to sub-confluence on collagen-coated plates in Roswell Park Memorial Institute Media (RPMI) 1640 supplemented with L-glutamine, and containing 10% horse serum, 5% fetal bovine serum (FBS), and 1% penicillin/streptomycin (Invitrogen, Burlington, Ontario), after which differentiation was induced for 24 hours with RPMI supplemented with 1% bovine serum albumin (BSA) fraction V and 50 ng/mL nerve growth factor (NGF) (Upstate Biotechnology, Waltham, Mass.). GST-RhoA63L pull downs were performed as described previously (Arthur et al., 2002). Briefly, after stimulation with AP-Nogo-66, cells were washed twice in ice cold Hepes-buffered saline (HBS), harvested in 1 mL of ice-cold lysis buffer containing 20 mM HEPES, pH 7.3, 150 mM NaCl, 5 mM $MgCl_2$, 1% (v/v) Triton X-100, 1 mM phenylmethylsulfonyl fluoride (PMSF), supplemented with Cømplete protease inhibitors (Roche Products, Laval, Quebec). GST-precleared lysates were then mixed with 30 µg of GST-RhoA63L fusion protein bound to sepharose beads for 1 hour at 4° C. Precipitated proteins were eluted with 2× sample buffer and analyzed by SDS-PAGE on a 4-15% gradient gel, followed by silver staining.

CRMP-RhoA Co-Immunoprecipitation Assays

HEK 293T cells were grown to sub-confluence and transfected with Lipofectamine 2000 according to manufacturer instructions (Invitrogen, Burlington, Ontario), washed twice with ice-cold PBS and lysed in lysis buffer A (50 mM Tris, pH 7.4, 150 mM NaCl, 1 mM EDTA, 1% (v/v) Triton X-100, 1 mM $Na_3VO_4$, 1 mM NaF, 1 mM PMSF and CØmplete protease inhibitors (Roche Diagnostics, Laval, PQ)). Lysates were pre-cleared with protein A/G-agarose (Santa Cruz Biotechnology, Santa Cruz, Calif.) and subjected to immunoprecipitation with myc-agarose or V5-agarose (Sigma Chemical Co., Oakville, Ontario). After washing 3 times with ice-cold PBS, bound protein was eluted with SDS and immunoblotted with anti-Myc (9E10, 1:1000; Sigma Chemical Co., Oakville, Ontario) or anti-V5 (1:5000; Invitrogen, Burlington, Ontario). For time course experiments, PC12 cells were transfected for 24 hours using Lipofectamine 2000 (Invitrogen, Burlington, Ontario) and differentiated with 50 ng/ml nerve growth factor (NGF; Upstate Biotechnology, Waltham, Mass.) for 24 hours. Cells were treated with Nogo-P4 peptide for the indicated period of time at 37° C. Cells were then lysed and proteins were immunoprecipitated as described above.

Far Western

Overlay of CRMP4 with RhoA was performed as previously described (McPherson et al., 1994). Briefly, HEK293T cell lysates transfected with CRMP4a-V5, CRMP4b-V5 or empty vector were subjected to immunoprecipitation with V5-agarose (Sigma Chemical Co., Oakville, Ontario). Immunoprecipitates were separated by SDS-PAGE, transferred to PVDF membranes and overlaid with 10 µg/ml of bacterially-purified RhoA for 1 hour at room temperature. RhoA was detected with a rabbit anti-RhoA antibody (Santa Cruz Biotechnology, Santa Cruz, Calif.).

Neurite outgrowth and Growth Cone Collapse Assays

For neurite outgrowth assays, myelin was dried down on poly-L-lysine-coated substrates. Substrates were washed and coated with 10 µg/ml laminin for 1 hr. For outgrowth on aggrecan, poly-L-lysine-coated substrates were coated with aggrecan and 10 µg/ml laminin for 2 hr at 37° C. Dissociated E13 chick DRG neurons were cultured in DRG media (F-12 medium, 10% FBS, 1% penicillin/streptomycin, 1%

L-glutamine, 50 ng/ml NGF) in the presence of virus for 24 hours, fixed with 4% paraformaldehyde/20% sucrose in PBS and double stained with anti-βIII tubulin (Covance, Berkeley, Calif.) and anti-V5 antibody (Sigma Chemical Co. Oakville, Ontario). Neurite outgrowth lengths per cell were assessed using Image J, a public domain JAVA image processing program as previously described (Fournier et al., 2003).

For growth cone collapse assays, chick E7 DRGs were cultured in DRG media for 18 hours on 4 well glass chamber slides sequentially coated with PLL and laminin as above. Sema3A-AP or AP conditioned media was prepared as described previously (Takahashi et al., 1998). Explants were stimulated with Sema3A-AP- or AP-conditioned media at indicated concentrations for 20 min and fixed with 4% paraformaldehyde, 20% sucrose and 0.1M $NaPO_4$. Explants were stained with rhodamine phalloidin and assessed for growth cone collapse as described (Luo et al., 1993).

CRMP-4 siRNA

For knockdown of CRMP-4a and CRMP4b, silencer pre-designed siRNA against rat CRMP-4 was used (siRNA ID: 48833; Ambion, Austin, Tex.). Controls were with a scrambled siRNA (CAGCAUGGUGGUACGCU-UGUAAGCA) (SEQ ID NO: 7) CRMP4b-targeted siRNA designed with the BLOCK-IT algorithm (Invitrogen, Burlington, Ontario). siRNAs were validated by co-transfecting siRNAs with CRMP4-V5 in HEK293T cells for 24 hours. Cell lysates were separated by SDS-PAGE and analyzed with an anti-V5 antibody. To validate siRNA efficacy in neurons, siRNA-transfected DRGs were co-infected with HSVCRMP4b-GFP. Twenty-four hours following infection GFP fluorescence was evaluated by fluorescence microscopy. For neurite outgrowth assays, P5 dissociated rat DRGs were prepared and seeded on laminin substrates as described previously (Hsieh et al., 2006). After 4 hours, DRGs were serum starved (in F-12 medium and 50 ng/ml NGF) and transfected with indicated siRNAs using Lipofectamine 2000. After 5 hours of transfection, media was replaced with fresh DRG media. Twenty-four hours following transfection, DRGs were removed from the plate with EDTA and re-seeded on myelin substrates. Neurons were left to grow for an additional 18 hours and processed for neurite outgrowth analysis as described above.

Immunofluorescence

E7-13 chick DRG explants were cultured in DRG media on poly-L-lysine- and laminin-coated substrates for 18 hours. For viral infections, recombinant viral preparations were added to the media 1 hour after plating. After 18 hours, cultures were treated with myelin and fixed with 4% paraformaldehyde/20% sucrose/PBS, permeabilized in 0.2% triton X-100 and double stained with polyclonal anti-RhoA antibody (Santa Cruz Biotechnology, Santa Cruz, Calif.) and anti-CRMP4b or V5 antibody. For filopodia and branch analysis, GFP and CRMP4bV5-infected growth cones were double stained with rhodamine-phalloidin (Molecular Probes, Eugene, Oreg.) and anti-V5 antibody. Filopodial length per growth cone was assessed using Image J, by measuring total filopodial length per growth cone averaged by the total number of filopodia per growth cone. Neurite branches were quantified by counting total branch buds per neurite.

Results a Novel Nogo-Dependent Interaction Between CRMP4B and RhoA

To identify molecules that functionally interact with RhoA to mediate neurite outgrowth inhibition, proteins that have enhanced affinity for a constitutively active, GTPase deficient mutant of RhoA were screened ((RhoA63L; Khosravi-Far et al., 1994) following treatment with Nogo-66, a potent inhibitory fragment of Nogo-A (GrandPre et al., 2000). Bacterially-purified glutathione-S-transferase-RhoA63L (GST-RhoA63L) was used as bait to precipitate proteins from PC12 cells following stimulation with Nogo-66 fused to alkaline phosphatase (AP-Nogo-66). PC12 cells were chosen for the biochemical screen based on their expression of MAI receptors (Hsieh et al., 2006), and their responsiveness to Nogo in neurite outgrowth assays (GrandPre et al., 2000) and biochemical assays evaluating RhoGTP levels (Fournier et al., 2003). Proteins interacting with GST-RhoA63L were separated by SDS-PAGE and visualized by silver staining. A 75 kDa protein with enhanced affinity for GST-RhoA63L following Nogo-66 treatment (FIG. 1a) was identified as CRMP4b by tandem mass spectrometry. The enhanced CRMP4-RhoA interaction was validated with a pan-CRMP antibody (provided by Dr. Peter McPherson, McGill University), which recognizes the 75 kDa CRMPb isoforms and the 65 kDa CRMPa isoforms (FIG. 1b). Both 75 kDa and 65 kDa CRMP isoform/s specifically precipitate with GST-RhoA63L while the interaction between the 75 kDa CRMPb isoform/s and RhoA is enhanced by Nogo stimulation (FIG. 1b).

Figure 2:
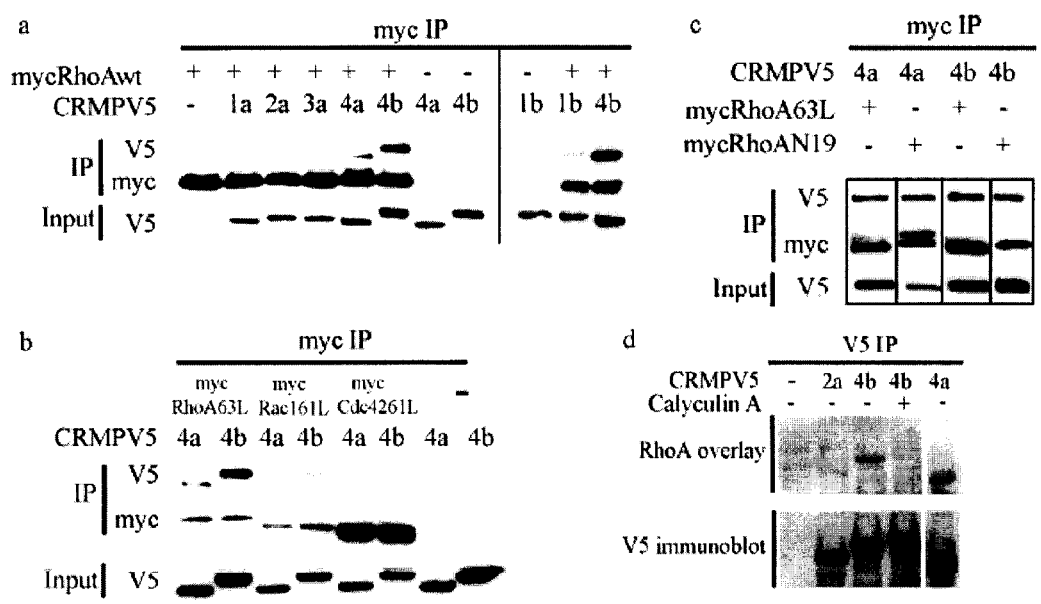
FIG. 2: The RhoA-CRMP4 interaction is highly specific, nucleotide-independent, phospho-dependent and direct. (a-c) HEK293T cells co-transfected with CRMP-V5 constructs and myc-tagged versions of wild type and mutant Rho GTPases and subjected to myc-immunoprecipitation. (a) CRMP4 preferentially binds to RhoA. Data from two separate blots are separated by a vertical line. (b) RhoA is the preferred binding partner for CRMP4. (c) CRMP4 binding to RhoA is nucleotide-independent. (d) CRMP-V5 was immunoprecipitated from control or Calyculin-treated HEK293T cells, separated by SDS-PAGE and overlayed with recombinant RhoA. RhoA binds directly to CRMP4a and CRMP4b but fails to bind to phosphorylated CRMP4b. IP, immunoprecipitation.

To assess the specificity of the CRMP4b-RhoA interaction, the ability of other CRMP members to interact with RhoA was analyzed. Wild type myc-RhoA and CRMP-V5 constructs were co-transfected in HEK293T cells. Myc-RhoA was immunoprecipitated from cell lysates and immune complexes were analyzed for CRMP-V5. RhoA interacts preferentially with CRMP4 family members with stronger binding to CRMP4b when compared to CRMP4a (FIG. 2a). RhoA fails to bind to other CRMPa isoforms and weakly associates with CRMP1b (FIG. 2a). Amino-terminally-tagged GFP-CRMP4b fails to associate with RhoA suggesting that amino-terminal tags interfere with this binding interaction (data not shown).

The specificity of the interaction between CRMP4 and RhoA was assessed through the binding of CRMP4 to Rac and Cdc42, two other members of the small Rho GTPases that regulate the actin cytoskeleton and positively regulate neurite outgrowth (Bishop and Hall, 2000). CRMP4a-V5 and CRMP4b-V5 were tested for binding to myc-tagged, GTP-bound active forms of RhoA (myc-RhoA63L), Rac1 (myc-Rac1Q61L) and Cdc42 (myc-Cdc42Q61L). CRMP4 binding to RhoA is markedly stronger than to Rac1 or Cdc42 (FIG. 2b). Similarly, CRMP4 binding to wild type and GDP-bound forms Rac and Cdc42 is negligible (data not shown). Taken together, these results demonstrate that both CRMP4a and CRMP4b specifically bind to RhoA with CRMP4b binding more strongly than CRMP4a.

CRMP4b-RhoA Binding is Nucleotide-Independent, Phospho-Dependent and Direct

Rho GTPases cycle between an inactive GDP-bound state and an active GTP-bound state. Downstream effectors of Rho GTPases bind to Rho GTPases in the active GTP-bound state while guanine nucleotide exchange factors prefer Rho GTPases in the nucleotide free or GTP-bound state (Hall, 1994). To study the nucleotide-dependence of the CRMP4-RhoA interaction, CRMP4 binding to constitutively active myc-RhoA63L or dominant negative myc-RhoAN19 was assessed (Feig and Cooper, 1988). CRMP4a-V5 and CRMP4b-V5 interact with both myc-RhoA63L and myc-RhoAN19 (FIG. 2c) indicating that the interaction between CRMP4 and RhoA is nucleotide-independent.

To assess if the binding interaction between CRMP4 and RhoA is direct, a RhoA overlay assay was performed on CRMP-V5 immunoprecipitated from 293T cells (FIG. 2d). RhoA specifically binds to CRMP4b-V5 and CRMP4a-V5 and fails to bind to CRMP2a-V5 in the overlay assay indicating that the interaction between CRMP4b and RhoA is direct and specific.

The phospho-dependence of the interaction was evaluated by stimulating CRMP4b-V5-expressing 293T cells with Calyculin A, a serine/threonine phosphatase inhibitor, prior to immunoprecipitating CRMP4b-V5. Calyculin-dependent CRMP4b-V5 phosphorylation is indicated by an upward mobility shift of the CRMP4b-V5 protein (FIG. 2d, V5 immunoblot). RhoA fails to bind to the phosphorylated species of CRMP4b-V5 in the overlay demonstrating that phosphorylated CRMP4b fails to bind to RhoA.

Nogo Specifically Modulates the CRMP4b-RhoA Interaction

To further define the specificity and the time course of the Nogo effect on the CRMP4b-RhoA interaction, PC12 cells were co-transfected with wild type myc-RhoA and CRMP4-V5 and stimulated with Nogo-P4 peptide, the minimal sequence of Nogo-66 required for Nogo-66-dependent responses (GrandPre et al., 2000). Myc-RhoA was immunoprecipitated and immune complexes were analyzed for CRMP4-V5. A rapid increase in CRMP4b-V5 immunoprecipitating with myc-RhoA is detected by 1 minute following Nogo stimulation, which is maintained by 10 minutes (FIG. 3a). Nogo stimulation does not regulate the interaction between myc-RhoA and CRMP4a-V5 (FIG. 3b). Similar results were obtained with AP-Nogo-66 stimulation and with the active form of RhoA (data not shown) suggesting that CRMP4b is regulated independently of Nogo-dependent RhoA cycling to the GTP-bound state. The Nogo-regulated RhoA-CRMP4b interaction was further confirmed by co-immunoprecipitation of endogenous proteins in Nogo-P4-treated P8 rat cerebellar cultures, where CRMP4b and RhoA form a complex 1 and 10 minutes following stimulation (FIG. 3c).

siRNA-Mediated Knockdown of CRMP4 Attenuates Neurite Outgrowth Inhibition

Figure 4:
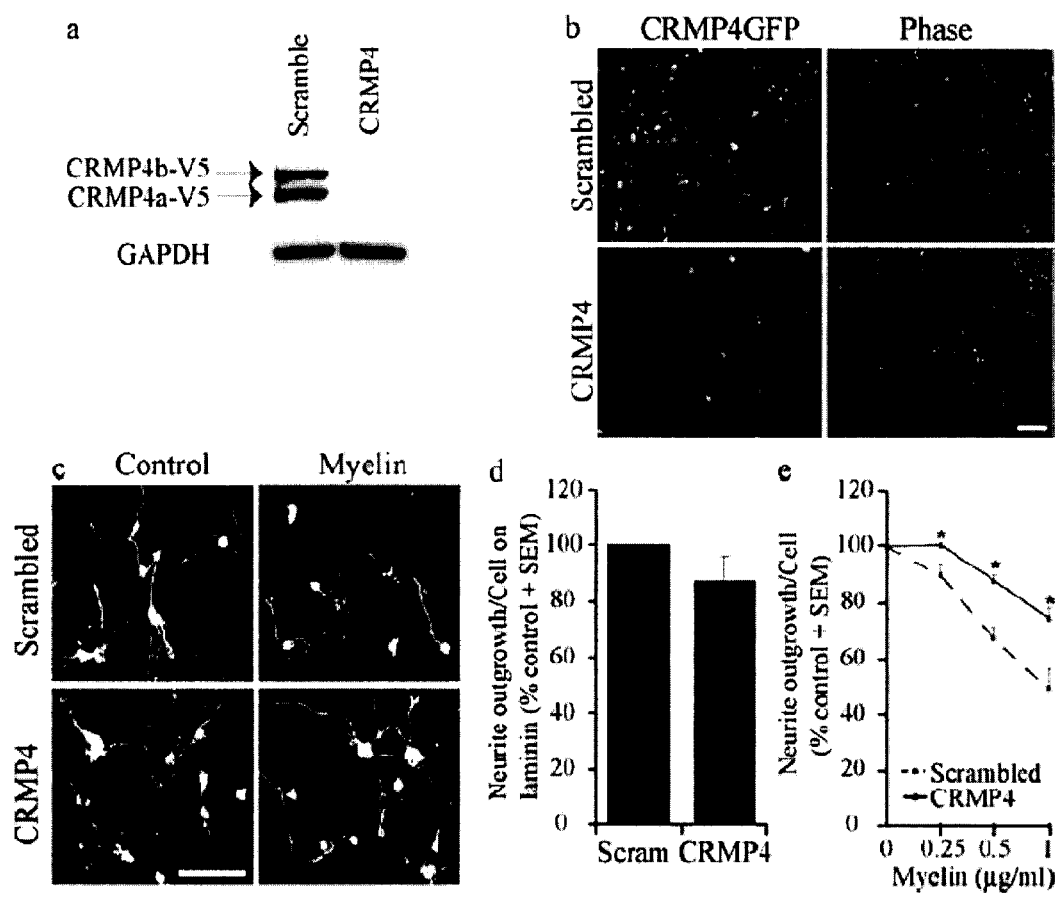
FIG. 4: siRNA-mediated knockdown of CRMP4 expression promotes neurite outgrowth on myelin. (a) HEK293T cells co-transfected with CRMP4-V5 and scrambled- or CRMP4-targeted siRNA and analyzed by immunoblotting with anti-V5 antibody. (b) Dissociated rat DRG neurons infected with HSVCRMP4b-GFP and transfected with scrambled or CRMP4 siRNA. Scale bar, 100 μm. (c) βIII tubulin-stained dissociated rat DRG neurons transfected with scrambled or CRMP4 siRNA and seeded on laminin (control) or myelin substrates for an 18 hour neurite outgrowth assay. Scale bar, 100 μm. (d) Quantitation of DRG outgrowth on control substrates with scrambled siRNA (Scram) or CRMP4 siRNA. (e) Quantitation of DRG neurite outgrowth on myelin from neurons transfected with scrambled or CRMP4 siRNA. Values are normalized to baseline outgrowth on the control laminin substrate for each experiment. Determinations are from 3 experiments performed in duplicate. *$p<0.01$ by student t-test compared to scrambled siRNA.
Figure 8:
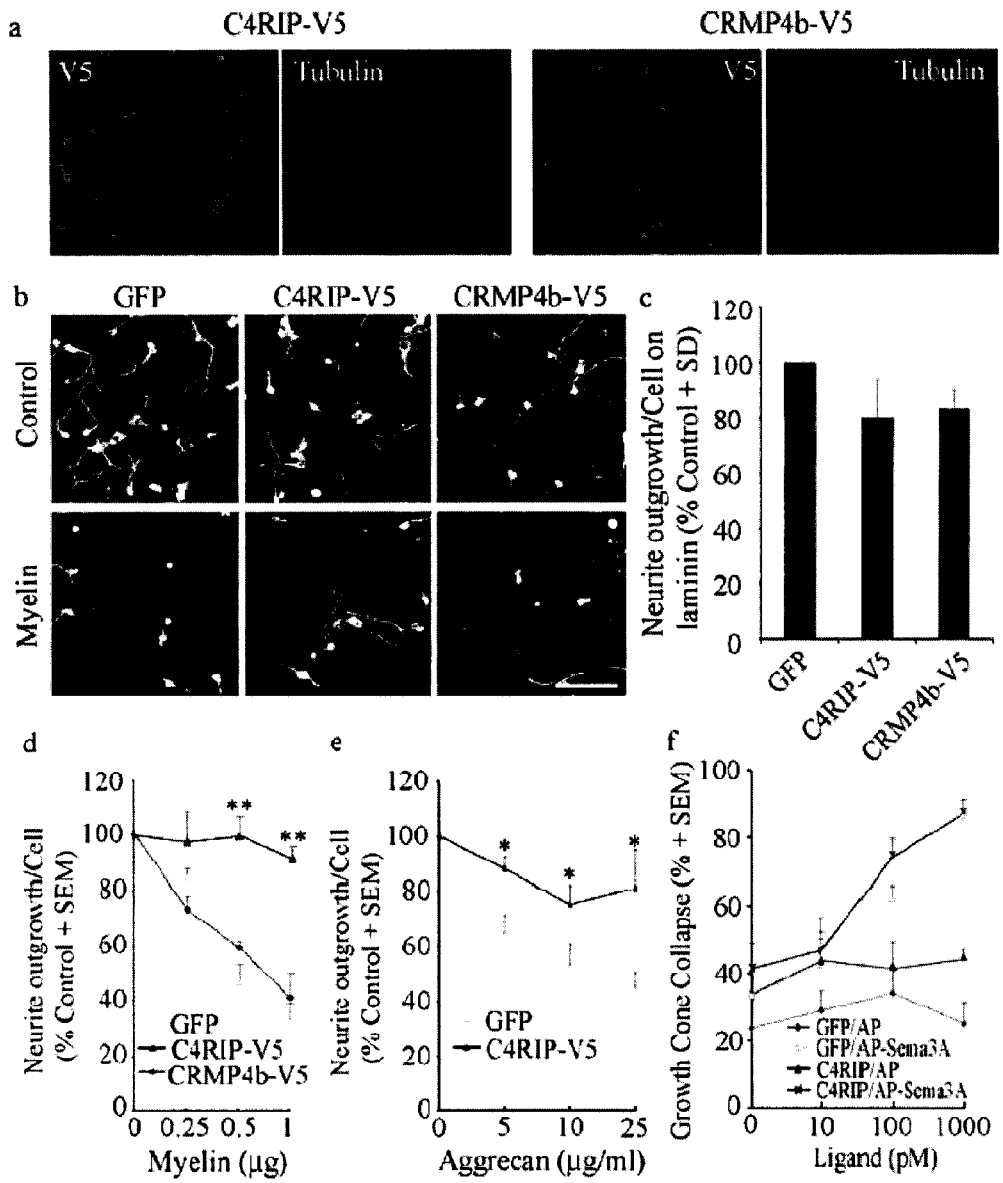
FIG. 8: C4RIP-V5 attenuates myelin inhibition. (a) E13 dissociated chick DRG neurons infected with HSV-C4RIP-V5 or HSV-CRMP4b-V5 and double-stained with anti-V5 and anti-βIII tubulin antibodies to validate neuronal infection. (b) E13 dissociated chick DRG neurons infected with C4RIP-V5 or CRMP4b-V5 plated on laminin (control) or myelin substrates and stained with anti-βIII tubulin to visualize neurite outgrowth. (c-e) Quantitation of neurite outgrowth from GFP-, C4RIP-, or CRMP4b-infected neurons on laminin (c), myelin (d) or aggrecan (e) substrates. In (c) neurite outgrowth per cell is normalized to outgrowth in GFP-infected neurons for each experiment (100%). In (d) and (e), neurite outgrowth is normalized to growth on the laminin substrate for each dose curve (100%). Determinations are from 4 separate experiments. Scale bar, 100 μm. *$p<0.05$ and **$p<0.01$ by student t-test compared to GFP. (f) Quantitation of growth cone collapse in E8 chick DRG neurons infected with HSV-GFP or HSV-C4RIP and stimulated for 20' with control AP ligand or AP-Sema3A ligand. Determinations are from 3 separate experiments performed in duplicate.

To determine if CRMP4 function is necessary for Nogo-dependent responses, neurite outgrowth on myelin substrates was assessed in the context of CRMP4-specific siRNA. The efficacy of CRMP4-specific siRNAs was validated in transfected 293T cells. One siRNA was identified, which robustly inhibits both CRMP4a and CRMP4b expression (FIG. 4a). Lipofectamine-mediated transfection of siRNAs efficiently targets P4 rat dorsal root ganglion neurons (DRGs) and CRMP4 siRNA introduced in this manner diminishes the expression of CRMP4b-GFP introduced by HSV-mediated infection (FIG. 4b). Rat DRGs were grown for 24 hours following siRNA transfection, removed from the substrate with EDTA and re-seeded on myelin substrates for an additional 18 hours. Rat DRG neuronal outgrowth is inhibited by approximately 50% on a substrate coated with 1 µg/ml of myelin using this protocol (FIG. 4e), a more modest inhibitory response than when dissociated DRG neurons are plated immediately on myelin substrates (FIG. 8; (Hsieh et al., 2006)). Neuronal outgrowth on the control laminin substrate is not significantly affected by the introduction of CRMP4 siRNA (FIG. 4d). However, CRMP4 siRNA-transfected P4 rat DRGs grow significantly better on myelin substrates than those transfected with scrambled siRNA (FIG. 4c, e) indicating that CRMP4 is necessary for myelin-dependent inhibition. The efficacy of the CRMP4 siRNA (FIG. 4e) may be underestimated due to the failure to transfect 100% of the DRG neurons (FIG. 4b).

CRMP4b Affects the Growth Cone Actin Cytoskeleton

Figure 5:
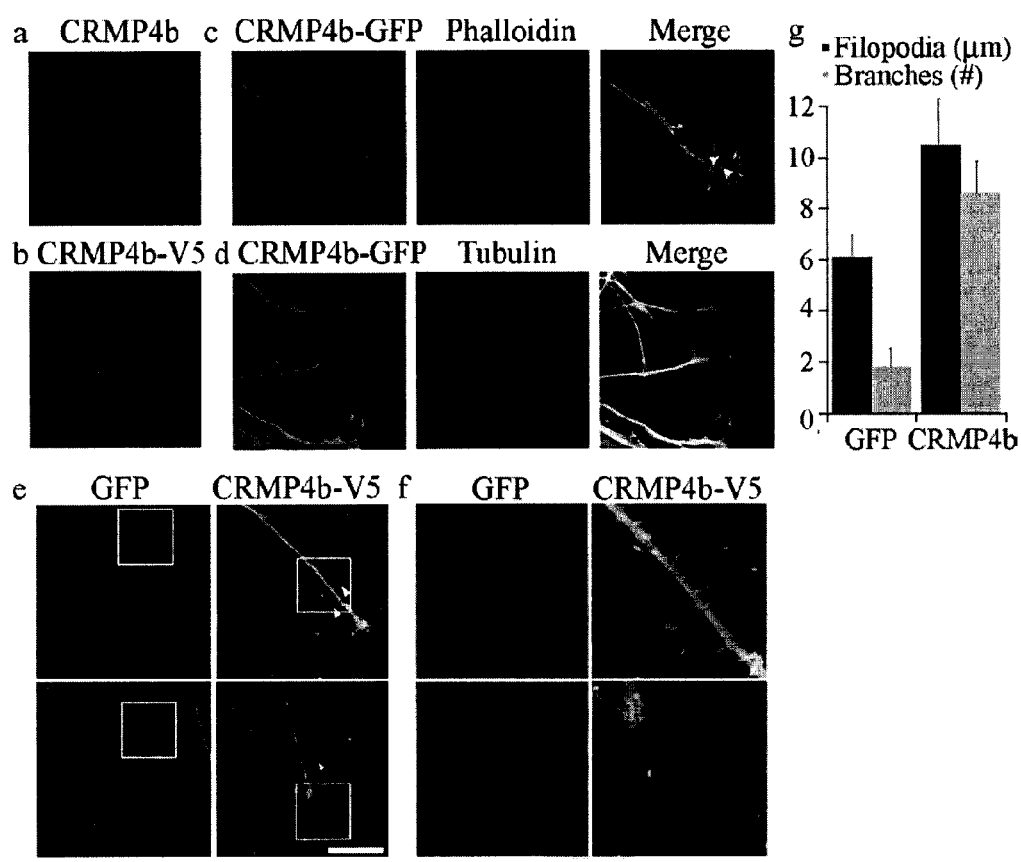
FIG. 5: CRMP4b overexpression promotes an actin-based filopodial phenotype in the neuronal growth cone and neurite. (a) E13 chick DRG stained with an anti-CRMP4b antibody. (b) E7 chick DRG neurons infected with HSV-CRMP4b-V5 and stained with anti-V5 antibody. (c-d) E7 chick DRG neurons infected with HSV-CRMP4b-GFP and double stained with rhodamine phalloidin (c) to label F-actin or anti-βIII tubulin antibody (d). (e) E13 chick DRG neurons infected with HSV-GFP or HSV-CRMP4b-V5. GFP and CRMP4b-infected growth cones were stained with rhodamine phalloidin (red). CRMP4b-V5 was stained with anti-V5 antibody (green). Scale bar, 10 μm. (f) Magnification of boxed regions in panel (d) demonstrating enhanced neurite branching and filopodial extension in CRMP4b-V5-infected DRG neurons. (g) Quantitation of number of branches per neurite and filopodial length in GFP- or CRMP4b-V5-infected DRG neurons.

CRMP proteins have been broadly implicated in the regulation of microtubule polymerization, actin bundling and endocytosis, three processes that influence growth cone dynamics and neurite outgrowth (Fukata et al., 2002b; Nishimura et al., 2003; Rosslenbroich et al., 2005). To gain insight into how CRMP4b may influence neurite outgrowth inhibition, the distribution of CRMP4b in DRG growth cones was assessed. As previously described, endogenous CRMP4b has a punctate pattern within the growth cone extending throughout the central and peripheral domains (FIG. 5a) (Quinn et al., 2003). CRMP4b-V5 (FIG. 5b) and CRMP4b-GFP (FIG. 5c, d) fusion proteins also label the entire growth cone with a less distinct punctate profile, likely due to elevated cytosolic CRMP4b levels in the overexpression paradigm. Carboxy-terminally tagged CRMP4b-GFP labels the growth cone more broadly than tubulin (FIG. 5d) and extends into the actin-rich peripheral domain (FIG. 5c) co-localizing with actin at a subset of punctae within the growth cone (FIG. 5c, arrows). Intriguingly, CRMP4b-V5 overexpression promotes the extension of filopodia from the growth cone that are on average 70% longer than filopodia in GFP-infected growth cones (FIG. 5e, f, g). This phenotype is also manifested in the DRG neurite where ectopic actin-rich branches are formed (FIG. 5 e, f, g; arrowheads). A similar phenotype was promoted by CRMP4b-GFP overexpression (data not shown). On average, 8 branches per neurite can be detected on CRMP4b-infected neurites compared to 2 branches per neurite on GFP-infected neurites (FIG. 5g). The localization of CRMP4b within the growth cone is consistent with a role in microtubule or actin dynamics. However, the filopodial and branching phenotypes promoted by CRMP4b overexpression suggest that CRMP4b may affect neuronal phenotype through an actin-based mechanism, an important observation since CRMPs have been implicated in modulating both microtubule and actin dynamics (Fukata et al., 2002a; Rosslenbroich et al., 2005). While the possibility that the fusion proteins may behave differently from native CRMP4b cannot be ruled out, both CRMP4b-V5 and CRMP4b-GFP have similar distributions to endogenous CRMP and promote similar growth cone phenotypes, suggesting that CRMP4b functionally interacts mainly with the actin cytoskeleton.

To further address the potential role for CRMP4b-RhoA complexes in neurite outgrowth inhibition, the distribution of CRMP4b and RhoA during Nogo-dependent growth cone collapse was examined. Uninfected and CRMP4b-V5-infected DRG growth cones were fixed and stained for endogenous RhoA and CRMP4b or the V5 epitope tag. Prior to stimulation, endogenous RhoA and CRMP4b have distinct distributions within the growth cone with negligible colocalization (FIG. 6a). In unstimulated (control) growth cones, overexpressed CRMP4b-V5 also has a distinct distribution compared to endogenous RhoA (FIG. 6b). Following myelin stimulation, RhoA and CRMP4b-V5 co-localize at a subset of distinct punctae within the growth cone central and peripheral domain (FIG. 6b, arrows) suggesting that a RhoA-CRMP4b complex forms in the growth cone where it may regulate actin cytoskeletal dynamics in response to inhibitory challenges.

C4RIP-V5 Attenuates CRMP4b-RhoA Binding

Figure 3:
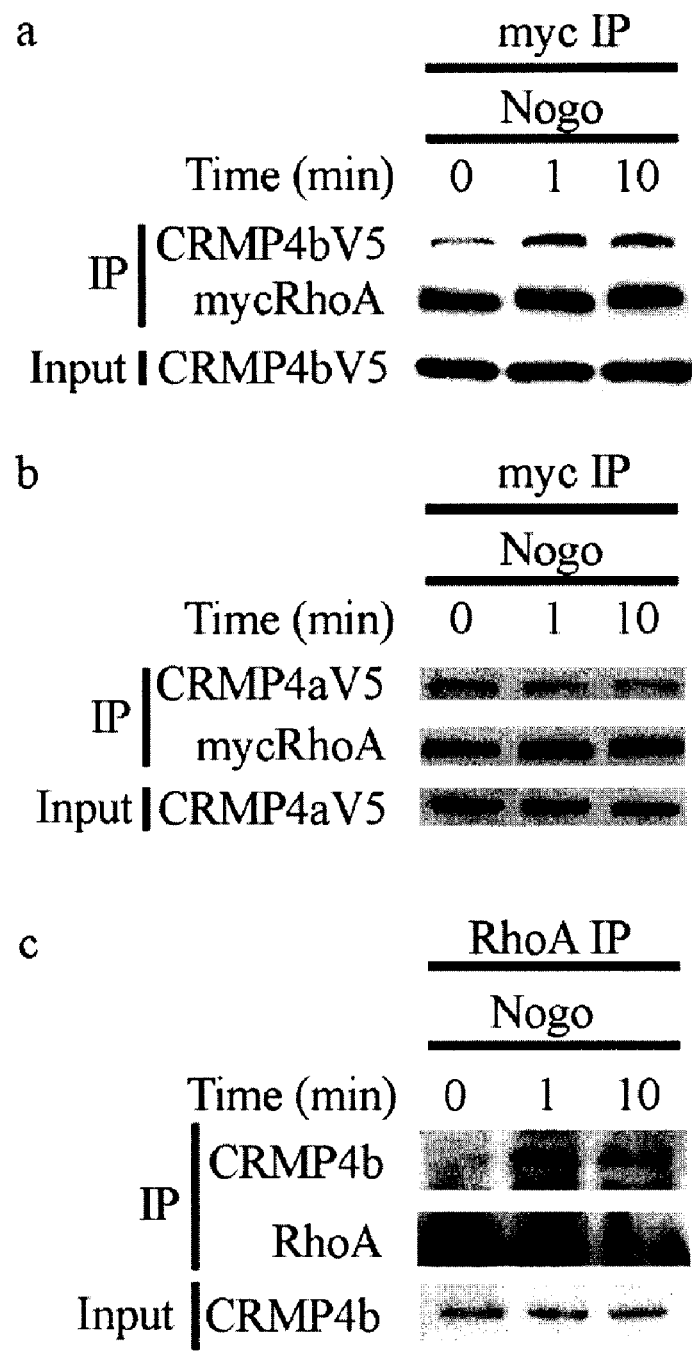
FIG. 3: Nogo-P4 peptide enhances the interaction between CRMP4b and RhoA. (a, b) PC12 cells transfected with myc-RhoA and CRMP4b-V5 (a) or CRMP4a-V5 (b) and, stimulated for 0, 1 or 10 minutes with Nogo-P4 peptide and subjected to myc-immunoprecipitation. (c) P8 rat cerebellar cultures stimulated with Nogo-P4 peptide, subjected to RhoA immunoprecipitation and analyzed for RhoA and CRMP4b. IP, immunoprecipitation.
Figure 7:
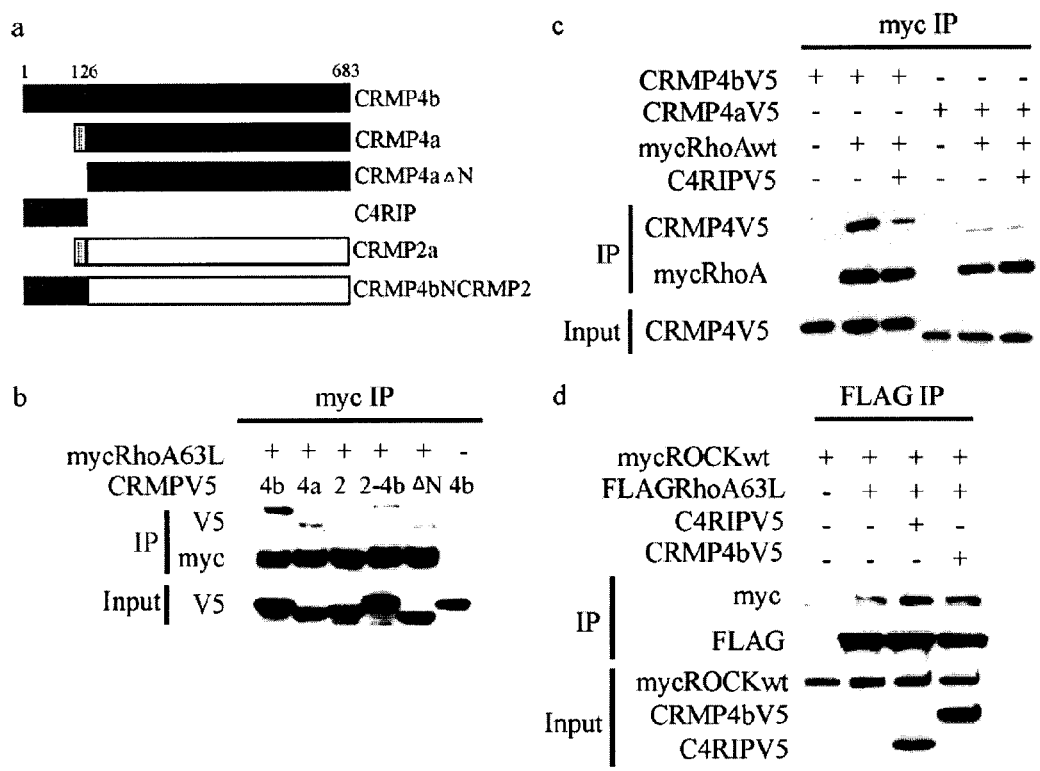
FIG. 7: The amino terminal domain of CRMP4b is sufficient for RhoA binding and disrupts full length CRMP4b-RhoA binding when expressed as a recombinant fusion protein. (a) Schematic of CRMP constructs generated to assess CRMP4 domains involved in RhoA binding. (b) HEK293T cells co-transfected with myc-RhoA63L and CRMP-V5 constructs described in (a) and subjected to myc-immunoprecipitation. (c) HEK293T cells co-transfected with myc-RhoAWT, CRMP4-V5 and C4RIP-V5 to assess the effect of C4RIP on full length CRMP4 binding to RhoA. (d) HEK293T cells co-transfected with FLAG-RhoA63L, myc-ROCK and C4RIP-V5 to assess the effect of C4RIP on RhoA binding to ROCK.

Nogo regulation of the CRMP4b-RhoA interaction raises the possibility that CRMP4b-RhoA complex formation is critical for inhibitory signaling. The specific enhancement of CRMP4b-RhoA binding suggests that the increased affinity may be mediated by the CRMP4b amino terminal extension. The ability of the CRMP4b amino terminus to mediate RhoA binding was therefore assessed. A chimeric CRMP molecule consisting of the CRMP4b amino terminus fused to CRMP2 (CRMP4bNCRMP2) was generated as well as a CRMP4 construct consisting of the common region of CRMP4a and CRMP4b (CRMP4aΔN; FIG. 7a). Both CRMP4bNCRMP2 and CRMP4aΔN co-immunoprecipitate with RhoA, however both proteins bind RhoA more weakly than full length CRMP4b (FIG. 7b). This indicates that two independent RhoA binding sites within the CRMP4b molecule are sufficient for RhoA binding and that the two sites may co-operate to mediate maximal RhoA binding; however the amino-terminal region of CRMP4b appears to be the critical site mediating Nogo-dependent recruitment to RhoA (FIG. 3).

To specifically disrupt the Nogo-dependent interaction between full length CRMP4b and RhoA, a construct was generated to express the unique amino terminal domain of CRMP4b (C4RIP-CRMP4b-RhoA Inhibitory Peptide; FIG. 7a) fused to a V5-epitope tag. As predicted, co-transfection of C4RIP-V5 significantly diminishes RhoA binding to full length CRMP4b without affecting binding to CRMP4a (FIG. 7c), presumably by competing for the RhoA binding site/s.

The specificity of C4RIP-V5 was then evaluated by examining its effect on binding between FLAG-RhoA63L and myc-Rho kinase (myc-ROCK), a critical RhoA effector molecule for myelin inhibition. C4RIP-V5 does not diminish binding between FLAG-RhoA63L and myc-ROCK (FIG. 7d). Similarly, overexpression of CRMP4b-V5 does not affect the binding between FLAG-RhoA63L and myc-ROCK indicating that CRMP4b does not alter the ability of RhoA to interact with this downstream effector.

C4RIP-V5 Attenuates Neurite Outgrowth Inhibition

The ability of C4RIP-V5 to attenuate CRMP4b-RhoA binding provides a valuable tool to determine if CRMP4b-RhoA complex formation is necessary for its role in myelin inhibition. CRMP4b-V5 or C4RIP-V5 was introduced into dissociated E13 chick DRG neurons via recombinant HSV virus (FIG. 8a) and neurite outgrowth was assessed on myelin substrates (FIG. 8b, d). CRMP4b-V5 is not sufficient to mimic myelin inhibitory responses (FIG. b, c), presumably due to its failure to increase its interaction with RhoA (FIG. 6b). C4RIP significantly attenuates myelin-dependent outgrowth inhibition compared to GFP- or full length CRMP4b-infected neurons (FIG. 8b, d). Unlike previously characterized Rho and ROCK antagonists, C4RIP does not promote basal DRG outgrowth on permissive control substrates (FIG. 8b, c; Lehmann et al., 1999; Fournier et al., 2003). DRG neurons infected with HSVC4RIP or with HSV-dominant negative ROCK (HSV-DNROCK; Alabed et al., 2006), are both protected from myelin inhibition; however, HSV-DN-ROCK promotes basal outgrowth by approximately 50%.

An advantage to targeting intracellular mediators of neurite outgrowth inhibition is their potential as convergent targets, which may attenuate multiple inhibitory influences. To evaluate if C4RIP-V5 may block additional inhibitory signals associated with CNS injury, the effect of C4RIP-V5 on neurite outgrowth inhibition mediated by aggrecan, an inhibitory chondroitin sulphate proteoglycan of the glial scar, was examined. Intriguingly, it was found that C4RIP also promotes neurite outgrowth on aggrecan (FIG. 8e).

To assess the specificity of C4RIP, its ability to block Sema3A-dependent growth cone collapse in E8 chick DRG neurons was tested. Sema3A-stimulation of neurons engages Rac1 GTPase and the CRMP2 isoform (Huber et al., 2003). It was found that C4RIP has no effect on Sema3A-dependent growth cone collapse (FIG. 8f). Taken together, these results indicate that disruption of the CRMP4b-RhoA interaction protects neurons from inhibitory influences that signal through RhoA GTPase.

Discussion

Regeneration following CNS trauma is limited by the activation of intracellular pathways within the injured neuron that block axonal extension through targeted modifications to the cytoskeleton (Hsieh et al., 2006). Development of antagonists to intracellular targets of axon outgrowth inhibitors is an effective approach to circumvent the inhibitory influence of the astroglial scar and MAIs (Dergham et al., 2002; Niederost et al., 2002; Borisoff et al., 2003; Fournier et al., 2003). Here, it was demonstrated that CRMP4b is a necessary intracellular mediator of neurite outgrowth inhibition. The present findings suggest that complex formation between CRMP4b and RhoA is critical for outgrowth inhibition and that this inhibition may be mediated through an actin-dependent phenotype. By targeting the critical CRMP4b-RhoA binding interaction, a competitive antagonist of CRMP4b-RhoA binding was developed which specifically promotes neurite outgrowth on inhibitory substrates suggesting an exciting new therapeutic target for nerve repair following CNS injury.

Dynamics of the CRMP4b-RhoA Interaction

The present invention describes a specific protein interaction between RhoA and CRMP4, which does not extend to other closely related family members of the Rho GTPases, nor to other CRMP family members. In the absence of Nogo stimulation the baseline interaction between endogenous CRMP4b and RhoA is negligible in cerebellar neurons and DRG growth cones. In transfected 293T and PC 2 cells, CRMP4b and RhoA do interact in the absence of Nogo; however, this interaction could be a function of protein overexpression.

Intriguingly, the RhoA-CRMP4b interaction is not dependent on the nucleotide binding state of RhoA, rather the interaction is dependent on the phosphorylation status of CRMP4. This raises the additional possibility that the strength of the baseline interaction may vary in different cells types as a function of the complement of kinases and phosphatases.

Figure 6:
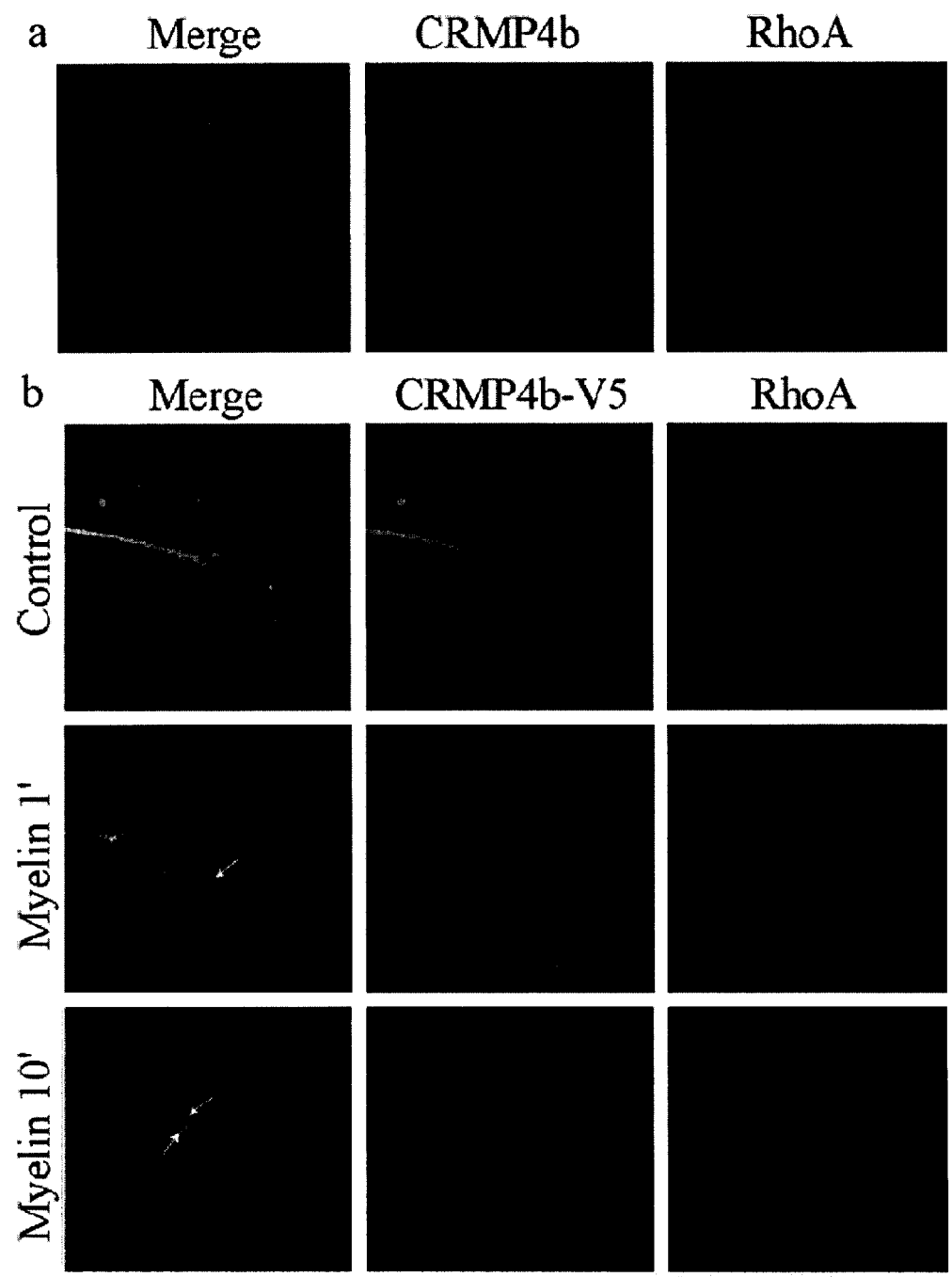
FIG. 6: CRMP4b and RhoA co-localize at discrete punctae during myelin-dependent growth cone collapse. Immuno-luorescent detection of endogenous CRMP4b and RhoA (a) or CRMP4b-V5 and RhoA (b) in control or myelin-stimulated E13 chick DRG growth cones. Arrows in the merged panels indicate areas of CRMP4b-V5-RhoA co-localization.

Since the RhoA used to screen for protein interactors was purified in bacteria, it is also conceivable that dephosphorylated RhoA is a favored binding partner for CRMP4b. This raises the possibility of a novel level of RhoA regulation in response to myelin inhibitors where the focus has largely been on the ability of MAIs to convert RhoA to the GTP-bound form (Dergham et al., 2002; Niederost et al., 2002; Fournier et al., 2003). This idea is consistent with finding that RhoA is phosphorylated at Ser188 by PKA and that RhoA phosphorylation modifies its binding to its endogenous inhibitor, Rho guanine nucleotide dissociation factor (RhoGDI) (Ellerbroek et al., 2003; Nusser et al., 2006). CRMP4 is subject to phosphorylation by glycogen synthase kinase-3β and dephosphorylation by PP2A phosphatase (Hill et al., 2006) and it is reasonable to hypothesize that phosphorylation alters its binding properties based on similarities to CRMP2 (Uchida et al., 2005). Together this suggests a model whereby Nogo-dependent engagement of a CRMP- and/or Rho-directed phosphatase may promote formation of a CRMP4b-RhoA complex. A prediction of this model would be that CRMP4b over-expression may fail to mimic myelin inhibition in DRG neurons because its association with RhoA is not adequately enhanced in the absence of appropriate post translational modifications, and this is what was observed (FIG. 6, 8).

Role of N-Terminal Variants of the CRMP Proteins

The recent discovery of novel amino-terminal variants of the original CRMP members in rat and in chick (Quinn et al., 2003; Yuasa-Kawada et al., 2003) has revealed additional potential functions for CRMPs. The unique amino-terminal extensions of the CRMPb isoforms could impart supplementary functions to each CRMP variant by mediating additional protein interactions. A reasonable possibility is that CRMP4a and CRMP4b are capable of mediating similar cytoskeletal rearrangements, however the amino terminal region of CRMP4b is necessary for recruitment to the appropriate cytoskeletal elements within the growth cone. This is consistent with the finding that overexpression of CRMP4b but not CRMP4a leads to an increase in neurite branching (Quinn et al., 2003).

C4RIP as a Therapeutic Agent

Targeting CRMP4-RhoA with C4RIP is a potential avenue for therapeutic intervention. The ability of C4RIP to attenuate inhibition in response to both MAIs and CSPGs is an obvious advantage in the complex inhibitory environment following CNS injury. The enrichment of CRMP expression in the nervous system raises the possibility that additional side effects on other cell types may be limited when compared to targeting ubiquitous molecules such as RhoA or ROCK. A unique characteristic of C4RIP is its failure to affect basal neurite outgrowth. This is believed to be the first example of an intracellular molecule, which can be specifically ascribed to an inhibitor-dependent neurite outgrowth pathway.

The Function of CRMP4b in Myelin-Dependent Inhibition

Reasonable hypotheses for CRMP4 function in myelin inhibition include effects on microtubule dynamics, actin dynamics and/or endocytosis. CRMP2 can bind to tubulin heterodimers and is an important organizer of microtubule assembly for establishing axon-dendrite fate during development (Fukata et al., 2002b; Arimura et al., 2005). This is partly mediated by binding to tubulin heterodimers and promoting microtubule assembly (Fukata et al., 2002b). In fact, CRMP2 undergoes ROCK-dependent phosphorylation in response to Nogo-66 and MAG and has been hypothesized to subsequently regulate microtubule dynamics (Mimura et al., 2006). Although all CRMP members can bind tubulin, CRMP4 is not a substrate for ROCK and no change in affinity between CRMP4 and tubulin in response to Nogo-66 stimulation was detected by co-immunoprecipitation analysis in PC 2 cells (data not shown). This suggests that Nogo-66 may not affect CRMP4-dependent microtubule dynamics; however, if the interaction is locally regulated within the neurite or growth cone, detection of this by co-immunoprecipitation may not have been possible.

The above data suggests that a CRMP4b-RhoA complex may participate in neurite outgrowth inhibition through actin-dependent processes. An association between CRMP4b and intersectin, an endocytic-exocytic adaptor protein (Quinn et al., 2003) raises the possibility that CRMP4b could play a role in regulating endocytosis. Endocytosis during neurite inhibition may be important for regulating membrane dynamics (Fournier et al., 2000), or may target the internalization of cell surface receptors or cell adhesion molecules enabling their temporal and spatial regulation in response to MAIs. A plausible model is one in which CRMP4b-RhoA complexes regulate localized actin rearrangements from the growth cone periphery to the central domain and subsequent endocytic events necessary for growth cone collapse and neurite withdrawal.

Although the present invention has been described hereinabove by way of preferred embodiments thereof, it can be modified without departing from the spirit, scope and nature of the subject invention, as defined in the appended claims.

LIST OF REFERENCES

1. Alabed Y Z, Grados-Munro E, Ferraro G B, Hsieh S, Fournier A E (2006) Neuronal responses to myelin are mediated by ROCK. J Neurochem 96:1616-1625.
2. Arimura N, Menager C, Kawano Y, Yoshimura T, Kawabata S, Hattori A, Fukata Y, Amano M, Goshima Y, Inagaki M, Morone N, Usukura J, Kaibuchi K (2005) Phosphorylation by Rho kinase regulates CRMP-2 activity in growth cones. Mol Cell Biol 25:9973-9984.
3. Arthur W T, Ellerbroek S M, Der C J, Burridge K, Wennerberg K (2002) XPLN, a guanine nucleotide exchange factor for RhoA and RhoB, but not RhoC. Journal of Biological Chemistry 277:42964-42972.
4. Bishop A L, Hall A (2000) Rho GTPases and their effector proteins. Biochem J 348 Pt 2:241-255.
5. Borisoff J F, Chan C C, Hiebert G W, Oschipok L, Robertson G S, Zamboni R, Steeves J D, Tetzlaff W (2003) Suppression of Rho-kinase activity promotes axonal growth on inhibitory CNS substrates. Mol Cell Neurosci 22:405-416.
6. Byk T, Dobransky T, Cifuentes-Diaz C, Sobel A (1996) Identification and molecular characterization of Unc-33-like phosphoprotein (Ulip), a putative mammalian homolog of the axonal guidance-associated unc-33 gene product. Journal of Neuroscience 16:688-701.
7. Chen M S, Huber A B, van der Haar M E, Frank M, Schnell L, Spillmann A A, Christ F, Schwab M E (2000) Nogo-A is a myelin-associated neurite outgrowth inhibitor and an antigen for monoclonal antibody IN-1. Nature 403:434-439.
8. Dergham P, Ellezam B, Essagian C, Avedissian H, Lubell W D, McKerracher L (2002) Rho signaling pathway targeted to promote spinal cord repair. J Neurosci 22:6570-6577.
9. Ellerbroek S M, Wennerberg K, Burridge K (2003) Serine phosphorylation negatively regulates RhoA in vivo. J Biol Chem 278:19023-19031.
10. Feig L A, Cooper G M (1988) Inhibition of NIH 3T3 cell proliferation by a mutant ras protein with preferential affinity for GDP. Mol Cell Biol 8:3235-3243.
11. Fournier A E, GrandPre T, Strittmatter S M (2001) Identification of a receptor mediating Nogo-66 inhibition of axonal regeneration. Nature 409:341-346.
12. Fournier A E, Takizawa B T, Strittmatter S M (2003) Rho Kinase inhibition enhances axonal regeneration in the injured CNS. J Neurosci 23:1416-1423.
13. Fournier A E, Nakamura F, Kawamoto S, Goshima Y, Kalb R G, Strittmatter S M (2000) Semaphorin3A enhances endocytosis at sites of receptor-F-actin colocalization during growth cone collapse. J Cell Biol 149:411-422.
14. Fournier A E, Takizawa B T, Strittmatter S M (2003) Rho Kinase inhibition enhances axonal regeneration in the injured CNS. J Neurosci 23: 1416-1423.
15. Fukata Y, Itoh T J, Kimura T, Menager C, Nishimura T, Shiromizu T, Watanabe H, Inagaki N, Iwamatsu A, Hotani H, Kaibuchi K (2002a) CRMP-2 binds to tubulin heterodimers to promote microtubule assembly. Nat Cell Biol 4:583-591.
16. Fukata Y, Itoh T J, Kimura T, Menager C, Nishimura T, Shiromizu T, Watanabe H, Inagaki N, Iwamatsu A, Hotani H, Kaibuchi K (2002b) CRMP-2 binds to tubulin heterodimers to promote microtubule assembly. Nature Cell Biology 4:583-591.
17. Gaetano C, Matsuo T, Thiele C J (1997) Identification and characterization of a retinoic acid-regulated human homologue of the unc-33-like phosphoprotein gene (hUlip) from neuroblastoma cells. J Biol Chem 272:12195-12201.
18. Goshima Y, Nakamura F, Strittmatter P, Strittmatter S M (1995) Collapsin-induced growth cone collapse mediated by an intracellular protein related to UNC-33. Nature 376: 509-514.
19. GrandPre T, Nakamura F, Vartanian T, Strittmatter S M (2000) Identification of the Nogo inhibitor of axon regeneration as a Reticulon protein. Nature 403:439-444.

20. Hall A (1994) Small GTP-binding proteins and the regulation of the actin cytoskeleton. Annu Rev Cell Biol 10:31-54.
21. Hedgecock E M, Culotti J G, Thomson J N, Perkins L A (1985) Axonal guidance mutants of *Caenorhabditis elegans* identified by filling sensory neurons with fluorescein dyes. Developmental Biology 111:158-170.
22. Hill J J, Callaghan D A, Ding W, Kelly J F, Chakravarthy B R (2006) Identification of okadaic acid-induced phosphorylation events by a mass spectrometry approach. Biochem Biophys Res Commun 342:791-799.
23. Hiraga A, Kuwabara S, Doya H, Kanai K, Fujitani M, Taniguchi J, Arai K, Mori M, Hattori T, Yamashita T. Rho-kinase inhibition enhances axonal regeneration after peripheral nerve injury. J. Peripher Nerv Syst. 2006 September; 11 (3):217-24.
24. Hsieh S, Ferraro G B, Fournier A E (2006) Myelin-associated inhibitors regulate cofilin phosphorylation and neuronal inhibition through Lim kinase and Slingshot phosphatase. J Neurosci 26:1006-1015.
25. Huber A, Kolodkin A, Ginty D, Cloutier J-F (2003) Signaling at the growth cone: Ligand-receptor complex and the control of axon growth and guidance. Ann Rev Neurosci 26:509-563.
26. Igarashi M, Strittmatter S M, Vartanian T, Fishman M C (1993) Mediation by G proteins of signals that cause collapse of growth cones. Science 259:77-79.
27. Inatome R, Tsujimura T, Hitomi T, Mitsui N, Hermann P, Kuroda S, Yamamura H, Yanagi S (2000) Identification of CRAM, a novel unc-33 gene family protein that associates with CRMP3 and protein-tyrosine kinase(s) in the developing rat brain. J Biol Chem 275:27291-27302.
28. Jurney W M, Gallo G, Letourneau P C, McLoon S C (2002) Rac1-mediated endocytosis during ephrin-A2- and semaphorin 3A-induced growth cone collapse. J Neurosci 22:6019-6028.
29. Khosravi-Far R, Chrzanowska-Wodnicka M, Solski P A, Eva A, Burridge K, Der C J (1994) Dbl and Vav mediate transformation via mitogen-activated protein kinase pathways that are distinct from those activated by oncogenic Ras. Mol Cell Biol 14:6848-6857.
30. Kottis V, Thibault P, Mikol D, Xiao Z C, Zhang R, Dergham P, Braun P E (2002) Oligodendrocyte-myelin glycoprotein (OMgp) is an inhibitor of neurite outgrowth. J Neurochem 82:1566-1569.
31. Lehmann M, Fournier A, Selles-Navarro I, Dergham P, Sebok A, Leclerc N, Tigyi G, McKerracher L (1999) Inactivation of Rho signaling pathway promotes CNS axon regeneration. J Neurosci 19:7537-7547.
32. Luo Y, Raible D, Raper J A (1993) Collapsin: a protein in brain that induces the collapse and paralysis of neuronal growth cones. Cell 75:217-227.
33. Mandemakers W J, Barres B A (2005) Axon regeneration: it's getting crowded at the gates of TROY. Curr Biol 15:R302-305.
34. Madure T, Kubo T, Tanag M, Matsude K, Tomita K, Yano K, Hosokawa K. The Rho-associated kinase inhibitor fasudil hydrochloride enhances neural regeneration after axotomy in the peripheral nervous system. Plast Reconstr Surg. 2007 February; 119 (2): 526-35.
35. McKerracher L, David S, Jackson D L, Kottis V, Dunn R J, Braun P E (1994) Identification of myelin-associated glycoprotein as a major myelin-derived inhibitor of neurite growth. Neuron 13:805-811.
36. McPherson P S, Czernik A J, Chilcote T J, Onofri F, Benfenati F, Greengard P, Schlessinger J, De Camilli P (1994) Interaction of Grb2 via its Src homology 3 domains with synaptic proteins including synapsin I. Proc Natl Acad Sci USA 91:6486-6490.
37. Mimura F, Yamagishi S, Arimura N, Fujitani M, Kubo T, Kaibuchi K, Yamashita T (2006) Myelin-associated Glycoprotein Inhibits Microtubule Assembly by a Rho-kinase-dependent Mechanism. J Biol Chem 281:15970-15979.
38. Minturn J E, Fryer H J, Geschwind D H, Hockfield S (1995) TOAD-64, a gene expressed early in neuronal differentiation in the rat, is related to unc-33, a *C. elegans* gene involved in axon outgrowth. Journal of Neuroscience 15:6757-6766.
39. Mukhopadhyay G, Doherty P, Walsh F S, Crocker P R, Filbin M T (1994) A novel role for myelin-associated glycoprotein as an inhibitor of axonal regeneration. Neuron 13:757-767.
40. Nakamura F, Tanaka M, Takahashi T, Kalb R G, Strittmatter S M (1998) Neuropilin-1 extracellular domains mediate semaphorin D/III-induced growth cone collapse. Neuron 21:1093-1100.
41. Neve R L, Howe J R, Hong S, Kalb R G (1997) Introduction of the glutamate receptor subunit 1 into motor neurons in vitro and in vivo using a recombinant herpes simplex virus. Neuroscience 79:435-447.
42. Niederost B, Oertle T, Fritsche J, McKinney R A, Bandtlow C E (2002) Nogo-A and myelin-associated glycoprotein mediate neurite growth inhibition by antagonistic regulation of RhoA and Rac1. J Neurosci 22:10368-10376.
43. Nishimura T, Fukata Y, Kato K, Yamaguchi T, Matsuura Y, Kamiguchi H, Kaibuchi K (2003) CRMP-2 regulates polarized Numb-mediated endocytosis for axon growth. Nature Cell Biology 5:819-826.
44. Nusser N, Gosmanova E, Makarova N, Fujiwara Y, Yang L, Guo F, Luo Y, Zheng Y, Tigyi G (2006) Serine phosphorylation differentially affects RhoA binding to effectors: implications to NGF-induced neurite outgrowth. Cell Signal 18:704-714.
45. Prinjha R, Moore S E, Vinson M, Blake S, Morrow R, Christie G, Michalovich D, Simmons D L, Walsh F S (2000) Inhibitor of neurite outgrowth in humans. Nature 403:383-384.
46. Quinn C C, Gray G E, Hockfield S (1999) A family of proteins implicated in axon guidance and outgrowth. Journal of Neurobiology 41:158-164.
47. Quinn C C, Chen E, Kinjo T G, Kelly G, Bell A W, Elliott R C, McPherson P S, Hockfield S (2003) TUC-4-b, a novel TUC family variant, regulates neurite outgrowth and associates with vesicles in the growth cone. Journal of Neuroscience 23:2815-2823.
48. Riento K, Ridley A J (2003) Rocks: multifunctional kinases in cell behaviour. Nat Rev Mol Cell Biol 4:446-456.
49. Rojas M, Donahue J P, Tan Z, Lin Y-Z (1998) Genetic engineering of proteins with cell membrane permeability Nature Biotechnology 16:370.
50. Rosslenbroich V, Dai L, Baader S L, Noegel A A, Gieselmann V, Kappler J (2005) Collapsin response mediator protein-4 regulates F-actin bundling. Exp Cell Res 310: 434-444.
51. Siddiqui S S, Culotti J G (1991) Examination of neurons in wild type and mutants of *Caenorhabditis elegans* using antibodies to horseradish peroxidase. Journal of Neurogenetics 7:193-211.
52. Suzuki Y, Nakagomi S, Namikawa K, Kiryu-Seo S, Inagaki N, Kaibuchi K, Aizawa H, Kikuchi K, Kiyama H (2003) Collapsin response mediator protein-2 accelerates axon regeneration of nerve-injured motor neurons of rat. Journal of Neurochemistry 86:1042-1050.

53. Takahashi T, Nakamura F, Jin Z, Kalb R G, Strittmatter S M (1998) Semaphorins A and E act as antagonists of neuropilin-1 and agonists of neuropilin-2 receptors. Nat Neurosci 1:487-493.
54. Uchida Y, Ohshima T, Sasaki Y, Suzuki H, Yanai S, Yamashita N, Nakamura F, Takei K, Ihara Y, Mikoshiba K, Kolattukudy P, Honnorat J, Goshima Y (2005) Semaphorin3A signalling is mediated via sequential Cdk5 and GSK3beta phosphorylation of CRMP2: implication of common phosphorylating mechanism underlying axon guidance and Alzheimer's disease. Genes Cells 10:165-179.
55. Wang K C, Koprivica V, Kim J A, Sivasankaran R, Guo Y, Neve R L, He Z (2002) Oligodendrocyte-myelin glycoprotein is a Nogo receptor ligand that inhibits neurite outgrowth. Nature 417:941-944.
56. Wang L H, Strittmatter S M (1997) Brain CRMP forms heterotetramers similar to liver dihydropyrimidinase. J Neurochem 69:2261-2269.
57. Wennerberg K, Ellerbroek S M, Liu R Y, Karnoub A E, Burridge K, Der C J (2002) RhoG signals in parallel with Rac1 and Cdc42. J Biol Chem 277:47810-47817.
58. Winton M J, Dubreuil C, Lasko D, Leclerc N, McKerracher L (2002) Characterization of New Cell Permeable C3-like Proteins that Inactivate Rho and Stimulate Neurite Outgrowth on Inhibitory Substrates J. Biol Chem 277: 32820-32829.
59. Yoshimura T, Kawano Y, Arimura N, Kawabata S, Kikuchi A, Kaibuchi K (2005) GSK-3beta regulates phosphorylation of CRMP-2 and neuronal polarity. Cell 120:137-149.
60. Yuasa-Kawada J, Suzuki R, Kano F, Ohkawara T, Murata M, Noda M (2003) Axonal morphogenesis controlled by antagonistic roles of two CRMP subtypes in microtubule organization. European Journal of Neuroscience 17:2329-2343.

The invention claimed is:

1. A purified polypeptide having the amino acid sequence of SEQ ID NO: 2, or an amino acid sequence having at least 98% identity to SEQ ID NO: 2.

2. A purified polypeptide as defined in claim 1, further comprising a membrane-translocating sequence (MTS).

3. A purified polypeptide having the amino acid sequence of SEQ ID NO: 2, or an amino acid sequence having at least 98% identity to SEQ ID NO: 2 further comprising a membrane-translocating sequence (MTS), wherein said MTS is encoded by the nucleotide sequence of SEQ ID NO: 10 or SEQ ID NO: 13.

* * * * *

SEQUENCE LISTING

<160> NUMBER OF SEQ ID NOS: 12

<210> SEQ ID NO 1
<211> LENGTH: 683
<212> TYPE: PRT
<213> ORGANISM: Rattus norvegicus

<400> SEQUENCE: 1

```
Met Ala Ser Gly Arg Arg Gly Trp Asp Ser Ser His Glu Asp Asp Leu
1               5                   10                  15

Pro Val Tyr Leu Ala Arg Pro Gly Thr Thr Asp Gln Val Pro Arg Gln
            20                  25                  30

Lys Tyr Gly Gly Met Phe Cys Asn Val Glu Gly Ala Phe Glu Ser Lys
        35                  40                  45

Thr Leu Asp Phe Asp Ala Leu Ser Val Gly Gln Arg Gly Ala Lys Thr
    50                  55                  60

Pro Arg Ser Ser Gln Gly Ser Gly Arg Gly Ala Gly Asn Arg Pro Gly
65                  70                  75                  80

Val Glu Gly Asp Thr Arg Arg Gly Pro Gly Arg Glu Glu Ser Arg Glu
                85                  90                  95

Pro Val Pro Glu Ser Pro Lys Pro Ala Gly Val Glu Ile Arg Ser Ala
            100                 105                 110

Thr Gly Lys Glu Val Leu Gln Asn Leu Gly Pro Lys Asp Lys Ser Asp
        115                 120                 125

Arg Leu Leu Ile Lys Gly Gly Arg Ile Val Asn Asp Asp Gln Ser Phe
    130                 135                 140

Tyr Ala Asp Ile Tyr Met Glu Asp Gly Leu Ile Lys Gln Ile Gly Asp
145                 150                 155                 160

Asn Leu Ile Val Pro Gly Gly Val Lys Thr Ile Glu Ala Asn Gly Lys
                165                 170                 175

Met Val Met Pro Gly Gly Ile Asp Val His Thr His Phe Gln Met Pro
            180                 185                 190

Tyr Lys Gly Met Thr Thr Val Asp Asp Phe Phe Gln Gly Thr Lys Ala
        195                 200                 205

Ala Leu Ala Gly Gly Thr Thr Met Ile Ile Asp His Val Val Pro Glu
    210                 215                 220

Pro Glu Ser Ser Leu Thr Glu Ala Tyr Glu Lys Trp Arg Glu Trp Ala
225                 230                 235                 240
```

```
Asp Gly Lys Ser Cys Cys Asp Tyr Ala Leu His Val Asp Ile Thr His
            245                 250                 255
Trp Asn Asp Ser Val Lys Gln Glu Val Gln Asn Leu Ser Lys Glu Lys
            260                 265                 270
Gly Val Asn Ser Phe Met Val Tyr Met Ala Tyr Lys Asp Leu Tyr Gln
            275                 280                 285
Val Ser Asn Thr Glu Leu Tyr Glu Ile Phe Thr Cys Leu Gly Glu Leu
            290                 295                 300
Gly Ala Ile Ala Gln Val His Ala Glu Asn Gly Asp Ile Ile Ala Gln
305                 310                 315                 320
Glu Gln Ala Arg Met Leu Glu Met Gly Ile Thr Gly Pro Glu Gly His
            325                 330                 335
Val Leu Ser Arg Pro Glu Glu Leu Glu Ala Glu Ala Val Phe Arg Ala
            340                 345                 350
Ile Thr Val Ala Ser Gln Thr Asn Cys Pro Leu Tyr Val Thr Lys Val
            355                 360                 365
Met Ser Lys Ser Ala Ala Asp Leu Ile Ser Gln Ala Arg Lys Lys Gly
            370                 375                 380
Asn Val Val Phe Gly Glu Pro Ile Thr Ala Ser Leu Gly Ile Asp Gly
385                 390                 395                 400
Thr His Tyr Trp Ser Lys Asn Trp Ala Lys Ala Ala Phe Val Thr
            405                 410                 415
Ser Pro Pro Leu Ser Pro Asp Pro Thr Thr Pro Asp Tyr Ile Asn Ser
            420                 425                 430
Leu Leu Ala Ser Gly Asp Leu Gln Leu Ser Gly Ser Ala His Cys Thr
            435                 440                 445
Phe Ser Thr Ala Gln Lys Ala Ile Gly Lys Asp Asn Phe Thr Ala Ile
            450                 455                 460
Pro Glu Gly Thr Asn Gly Val Glu Glu Arg Met Ser Val Ile Trp Asp
465                 470                 475                 480
Lys Ala Val Ala Thr Gly Lys Met Asp Glu Asn Gln Phe Val Ala Val
            485                 490                 495
Thr Ser Thr Asn Ala Ala Lys Ile Phe Asn Leu Tyr Pro Arg Lys Gly
            500                 505                 510
Arg Ile Ala Val Gly Ser Asp Ser Asp Leu Val Ile Trp Asp Pro Asp
            515                 520                 525
Ala Val Lys Ile Val Ser Ala Lys Asn His Gln Ser Val Ala Glu Tyr
            530                 535                 540
Asn Ile Phe Glu Gly Met Glu Leu Arg Gly Ala Pro Leu Val Val Ile
545                 550                 555                 560
Cys Gln Gly Lys Ile Met Leu Glu Asp Gly Asn Leu His Val Thr Gln
            565                 570                 575
Gly Ala Gly Arg Phe Ile Pro Cys Ser Pro Phe Ser Asp Tyr Val Tyr
            580                 585                 590
Lys Arg Ile Lys Ala Arg Arg Lys Met Ala Asp Leu His Ala Val Pro
            595                 600                 605
Arg Gly Met Tyr Asp Gly Pro Val Phe Asp Leu Thr Thr Pro Lys
            610                 615                 620
Gly Gly Thr Pro Ala Gly Ser Thr Arg Gly Ser Pro Thr Arg Pro Asn
625                 630                 635                 640
Pro Pro Val Arg Asn Leu His Gln Ser Gly Phe Ser Leu Ser Gly Thr
            645                 650                 655
Gln Val Asp Glu Gly Val Arg Ser Ala Ser Lys Arg Ile Val Ala Pro
```

```
                 660               665                670
Pro Gly Gly Arg Ser Asn Ile Thr Ser Leu Ser
            675                 680

<210> SEQ ID NO 2
<211> LENGTH: 126
<212> TYPE: PRT
<213> ORGANISM: Rattus norvegicus

<400> SEQUENCE: 2

Met Ala Ser Gly Arg Arg Gly Trp Asp Ser Ser His Glu Asp Asp Leu
1               5                   10                  15

Pro Val Tyr Leu Ala Arg Pro Gly Thr Thr Asp Gln Val Pro Arg Gln
            20                  25                  30

Lys Tyr Gly Gly Met Phe Cys Asn Val Glu Gly Ala Phe Glu Ser Lys
        35                  40                  45

Thr Leu Asp Phe Asp Ala Leu Ser Val Gly Gln Arg Gly Ala Lys Thr
    50                  55                  60

Pro Arg Ser Ser Gln Gly Ser Gly Arg Gly Ala Gly Asn Arg Pro Gly
65                  70                  75                  80

Val Glu Gly Asp Thr Arg Arg Gly Pro Gly Arg Glu Glu Ser Arg Glu
                85                  90                  95

Pro Val Pro Glu Ser Pro Lys Pro Ala Gly Val Glu Ile Arg Ser Ala
            100                 105                 110

Thr Gly Lys Glu Val Leu Gln Asn Leu Gly Pro Lys Asp Lys
        115                 120                 125

<210> SEQ ID NO 3
<211> LENGTH: 2052
<212> TYPE: DNA
<213> ORGANISM: Rattus norvegicus

<400> SEQUENCE: 3
atggcttcgg gccgaagggg ttgggacagc tcccacgagg acgacctgcc tgtgtacttg      60
gcccggccgg gcaccacaga tcaggtccca cggcagaagt acgtggcat gttctgcaac     120 gtggagggcg ccttcgagag caagacattg gattttgatg ccctgagtgt gggacagcgc     180
ggcgccaaaa ctccccggag cagccagggc agcggccgcg gcgcggggaa ccggcccggg     240
gtggaagggg acacgcgcag gggcccgggc cgggaggaga gcagggagcc cgtgcctgag     300
tcgcccaagc ccgccggggt agagatccgg agcgccactg gcaaggaggt cttgcagaac     360
ctcggtccca aggacaagag tgaccgtctt ctaatcaagg agggagaat cgtcaacgat     420 gatcagtcct tttatgctga tatttacatg gaggatggct tgataaagca aattggagac     480
aatctgattg tccctggagg tgtgaagacc attgaggcca tgggaagat ggtgatgcct     540 ggaggcattg atgtccatac ccacttccag atgccttaca gggatgac acagtggac     600 gatttcttcc aagggacaaa ggctgcctta gcgggaggaa ccaccatgat cattgaccat     660
gtggtacctg aacctgagtc tagcctgacc gaggcctatg aaaagtggcg tgagtgggct     720
gacgggaaga gctgctgtga ctatgctttg catgtggaca tcacccactg gaatgacagc     780
gtcaagcaag aggtgcagaa cctcagtaag gaaaaggcg ttaactcctt catggtttac     840
atggcataca aggatttata tcaagtgtcc aacacagagc tctatgagat cttcacctgc     900
ctgggagaac tgggggccat tgctcaagtt catgccgaga tggagacat cattgcccag     960 gagcaggcac gaatgctgga aatgggaata acaggcccag aaggtcatgt tctgagcaga    1020
ccggaagagc tggaagctga ggctgtgttc cgtgccatca ccgtcgccag ccagaccaac    1080
```

```
tgcccccttt atgtcaccaa ggtcatgagc aagagcgcgg ctgatctcat ctcacaagcc      1140
aggaagaaag gaaatgtggt ctttggcgag cccatcactg ccagcctggg aatagatgga      1200
acccattact ggagtaagaa ctgggccaag gcagctgcat ttgtgacatc cccacctctg      1260
agccctgacc caaccacacc tgactacatc aactccttgc tggccagtgg agatctgcag      1320
ctctctggaa gtgcccactg taccttcagc actgcccaga agccattgg gaaggacaac       1380 ttcacggcta tccctgaggg caccaatggc gtggaggagc gtatgtctgt catctgggac      1440
aaggctgtgg ccacagggaa gatggatgaa aaccagtttg tggctgtgac aagtaccaac      1500
gctgccaaga tattcaacct gtaccctcgc aaggggagaa tagctgtggg ttctgacagc      1560
gaccttgtca tctgggatcc agatgccgtg aagatcgtct ctgccaagaa ccaccagtcg      1620
gttgcggaat acaacatctt tgaagggatg gagctgcgtg gggcacctct ggtggttatc      1680
tgccagggca agatcatgct ggaagatggt aacctgcacg tgacccaggg ggccggccgc      1740
ttcattccct gcagcccatt ctctgactat gtctataagc gcattaaagc aaggaggaag      1800
atggcggacc tgcatgcagt cccaagaggc atgtatgatg accagtgtt tgacttgacc       1860 accaccccca agggggcac cccagctggc tctactcgag gctctcccac tcggccaaac       1920
ccaccagtga ggaacctcca tcagtcggga tttagtctgt caggcaccca agtggatgag      1980
ggtgtccgct cagccagcaa acgcattgtg gcgcccctg aggccgttc taacatcaca        2040 tccctgagtt aa                                                          2052

<210> SEQ ID NO 4
<211> LENGTH: 378
<212> TYPE: DNA
<213> ORGANISM: Rattus norvegicus

<400> SEQUENCE: 4
atggcttcgg gccgaagggg ttgggacagc tcccacgagg acgacctgcc tgtgtacttg       60
gcccggccgg gcaccacaga tcaggtccca cggcagaagt acggtggcat gttctgcaac      120
gtggagggcg ccttcgagag caagacattg gattttgatg ccctgagtgt gggacagcgc      180
ggcgccaaaa ctccccggag cagccagggc agcggccgcg gcgcggggaa ccggcccggg      240
gtggaagggg acacgcgcag gggcccgggc cgggaggaga gcaggagcc cgtgcctgag       300 tcgcccaagc ccgccggggt agagatccgg agcgccactg gcaaggaggt cttgcagaac      360
ctcggtccca aggacaag                                                    378

<210> SEQ ID NO 5
<211> LENGTH: 570
<212> TYPE: PRT
<213> ORGANISM: Rattus norvegicus

<400> SEQUENCE: 5

Met Ser Tyr Gln Gly Lys Lys Asn Ile Pro Arg Ile Thr Ser Asp Arg
1               5                   10                  15

Leu Leu Ile Lys Gly Gly Arg Ile Val Asn Asp Asp Gln Ser Phe Tyr
            20                  25                  30

Ala Asp Ile Tyr Met Glu Asp Gly Leu Ile Lys Gln Ile Gly Asp Asn
        35                  40                  45

Leu Ile Val Pro Gly Gly Val Lys Thr Ile Glu Ala Asn Gly Lys Met
    50                  55                  60

Val Met Pro Gly Gly Ile Asp Val His Thr His Phe Gln Met Pro Tyr
65                  70                  75                  80
```

```
Lys Gly Met Thr Thr Val Asp Asp Phe Phe Gln Gly Thr Lys Ala Ala
            85                  90                  95

Leu Ala Gly Gly Thr Thr Met Ile Ile Asp His Val Val Pro Glu Pro
        100                 105                 110

Glu Ser Ser Leu Thr Glu Ala Tyr Glu Lys Trp Arg Glu Trp Ala Asp
            115                 120                 125

Gly Lys Ser Cys Cys Asp Tyr Ala Leu His Val Asp Ile Thr His Trp
        130                 135                 140

Asn Asp Ser Val Lys Gln Glu Val Gln Asn Leu Ser Lys Glu Lys Gly
145                 150                 155                 160

Val Asn Ser Phe Met Val Tyr Met Ala Tyr Lys Asp Leu Tyr Gln Val
                165                 170                 175

Ser Asn Thr Glu Leu Tyr Glu Ile Phe Thr Cys Leu Gly Leu Gly
            180                 185                 190

Ala Ile Ala Gln Val His Ala Glu Asn Gly Asp Ile Ile Ala Gln Glu
        195                 200                 205

Gln Ala Arg Met Leu Glu Met Gly Ile Thr Gly Pro Glu Gly His Val
        210                 215                 220

Leu Ser Arg Pro Glu Glu Leu Glu Ala Glu Ala Val Phe Arg Ala Ile
225                 230                 235                 240

Thr Val Ala Ser Gln Thr Asn Cys Pro Leu Tyr Val Thr Lys Val Met
            245                 250                 255

Ser Lys Ser Ala Ala Asp Leu Ile Ser Gln Ala Arg Lys Lys Gly Asn
            260                 265                 270

Val Val Phe Gly Glu Pro Ile Thr Ala Ser Leu Gly Ile Asp Gly Thr
        275                 280                 285

His Tyr Trp Ser Lys Asn Trp Ala Lys Ala Ala Ala Phe Val Thr Ser
        290                 295                 300

Pro Pro Leu Ser Pro Asp Pro Thr Thr Pro Asp Tyr Ile Asn Ser Leu
305                 310                 315                 320

Leu Ala Ser Gly Asp Leu Gln Leu Ser Gly Ser Ala His Cys Thr Phe
            325                 330                 335

Ser Thr Ala Gln Lys Ala Ile Gly Lys Asp Asn Phe Thr Ala Ile Pro
            340                 345                 350

Glu Gly Thr Asn Gly Val Glu Glu Arg Met Ser Val Ile Trp Asp Lys
            355                 360                 365

Ala Val Ala Thr Gly Lys Met Asp Glu Asn Gln Phe Val Ala Val Thr
        370                 375                 380

Ser Thr Asn Ala Ala Lys Ile Phe Asn Leu Tyr Pro Arg Lys Gly Arg
385                 390                 395                 400

Ile Ala Val Gly Ser Asp Ser Asp Leu Val Ile Trp Asp Pro Asp Ala
            405                 410                 415

Val Lys Ile Val Ser Ala Lys Asn His Gln Ser Val Ala Glu Tyr Asn
            420                 425                 430

Ile Phe Glu Gly Met Glu Leu Arg Gly Ala Pro Leu Val Val Ile Cys
        435                 440                 445

Gln Gly Lys Ile Met Leu Glu Asp Gly Asn Leu His Val Thr Gln Gly
        450                 455                 460

Ala Gly Arg Phe Ile Pro Cys Ser Pro Phe Ser Asp Tyr Val Tyr Lys
465                 470                 475                 480

Arg Ile Lys Ala Arg Arg Lys Met Ala Asp Leu His Ala Val Pro Arg
            485                 490                 495

Gly Met Tyr Asp Gly Pro Val Phe Asp Leu Thr Thr Pro Lys Gly
            500                 505                 510
```

Gly Thr Pro Ala Gly Ser Thr Arg Gly Ser Pro Thr Arg Pro Asn Pro
        515                 520                 525

Pro Val Arg Asn Leu His Gln Ser Gly Phe Ser Leu Ser Gly Thr Gln
        530                 535                 540

Val Asp Glu Gly Val Arg Ser Ala Ser Lys Arg Ile Val Ala Pro Pro
545                 550                 555                 560

Gly Gly Arg Ser Asn Ile Thr Ser Leu Ser
                565                 570

<210> SEQ ID NO 6
<211> LENGTH: 1713
<212> TYPE: DNA
<213> ORGANISM: Rattus norvegicus

<400> SEQUENCE: 6

| | | | |
|---|---|---|---|
| atgtcctacc agggcaagaa gaacattcct cggatcacga gtgaccgtct tctaatcaag | 60 |
| ggagggagaa tcgtcaacga tgatcagtcc ttttatgctg atatttacat ggaggatggc | 120 |
| ttgataaagc aaattggaga caatctgatt gtccctggag gtgtgaagac cattgaggcc | 180 |
| aatgggaaga tggtgatgcc tggaggcatt gatgtcccata cccacttcca gatgccttac | 240 |
| aaggggatga ccacagtgga cgatttcttc aagggacaa aggctgcctt agcgggagga | 300 |
| accaccatga tcattgacca tgtggtacct gaacctgagt ctagcctgac cgaggcctat | 360 |
| gaaaagtggc gtgagtgggc tgacgggaag agctgctgtg actatgcttt gcatgtggac | 420 |
| atcacccact ggaatgacag cgtcaagcaa gaggtgcaga acctcagtaa ggaaaaaggc | 480 |
| gttaactcct tcatggttta catggcatac aaggatttat atcaagtgtc caacacagag | 540 |
| ctctatgaga tcttcacctg cctgggagaa ctggggggcca ttgctcaagt tcatgccgag | 600 |
| aatggagaca tcattgccca ggagcaggca cgaatgctgg aaatgggaat aacaggccca | 660 |
| gaaggtcatg ttctgagcag accggaagag ctggaagctg aggctgtgtt ccgtgccatc | 720 |
| accgtcgcca gccagaccaa ctgccccctt tatgtcacca aggtcatgag caagagcgcg | 780 |
| gctgatctca tctcacaagc caggaagaaa ggaaatgtgg tctttggcga gcccatcact | 840 |
| gccagcctgg aatagatgg aacccattac tggagtaaga actgggccaa ggcagctgca | 900 |
| tttgtgacat cccccacctct gagccctgac ccaaccacac tgactacat caactccttg | 960 |
| ctggccagtg gagatctgca gctctctgga agtgcccact gtaccttcag cactgcccag | 1020 |
| aaagccattg gaaggacaa cttcacggct atccctgagg gcaccaatgg cgtggaggag | 1080 |
| cgtatgtctg tcatctggga caaggctgtg gccacaggga gatggatga aaaccagttt | 1140 |
| gtggctgtga caagtaccaa cgctgccaag atattcaacc tgtaccctcg caaggggaga | 1200 |
| atagctgtgg ttctgacag cgaccttgtc atctgggatc cagatgccgt gaagatcgtc | 1260 |
| tctgccaaga ccaccagtc ggttgcggaa tacaacatct ttgaagggat ggagctgcgt | 1320 |
| ggggcacctc tggtggttat ctgccagggc aagatcatgc tggaagatgg taacctgcac | 1380 |
| gtgacccagg gggccggccg cttcattccc tgcagcccat tctctgacta tgtctataag | 1440 |
| cgcattaaag caaggaggaa gatggcggac ctgcatgcag tcccaagagg catgtatgat | 1500 |
| ggaccagtgt ttgacttgac caccaccccc aaggggggca ccccagctgg ctctactcga | 1560 |
| ggctctccca ctcggccaaa cccaccagtg aggaacctcc atcagtcggg atttagtctg | 1620 |
| tcaggcaccc aagtggatga gggtgtccgc tcagccagca acgcattgt ggcgcccct | 1680 |
| ggaggccgtt ctaacatcac atccctgagt taa | 1713 |

<210> SEQ ID NO 7
<211> LENGTH: 447
<212> TYPE: DNA
<213> ORGANISM: Rattus norvegicus

<400> SEQUENCE: 7

```
ggatccatgg cttcgggccg aaggggttgg gacagctccc acgaggacga cctgcctgtg      60
tacttggccc ggccgggcac cacagatcag gtcccacggc agaagtacgg tggcatgttc     120
tgcaacgtgg agggcgcctt cgagagcaag acattggatt ttgatgccct gagtgtggga     180
cagcgcggcg ccaaaaactcc ccggagcagc cagggcagcg gccgcggcgc ggggaaccgg     240
cccggggtgg aaggggacac gcgcagggc  ccgggccggg aggagagcag ggagcccgtg     300
cctgagtcgc ccaagcccgc cggggtagag atccggagcg ccactggcaa ggaggtcttg     360
cagaacctcg gtcccaagga caaggaattc gtgatgaatc ccgcaaacgc gcaaggcaga     420
catacacccg gtaccagact cctcgag                                         447
```

<210> SEQ ID NO 8
<211> LENGTH: 146
<212> TYPE: PRT
<213> ORGANISM: Rattus norvegicus

<400> SEQUENCE: 8

```
Met Ala Ser Gly Arg Arg Gly Trp Asp Ser Ser His Glu Asp Asp Leu
1               5                   10                  15

Pro Val Tyr Leu Ala Arg Pro Gly Thr Thr Asp Gln Val Pro Arg Gln
            20                  25                  30

Lys Tyr Gly Gly Met Phe Cys Asn Val Glu Gly Ala Phe Glu Ser Lys
        35                  40                  45

Thr Leu Asp Phe Asp Ala Leu Ser Val Gly Gln Arg Gly Ala Lys Thr
    50                  55                  60

Pro Arg Ser Ser Gln Gly Ser Gly Arg Gly Ala Gly Asn Arg Pro Gly
65                  70                  75                  80

Val Glu Gly Asp Thr Arg Arg Gly Pro Gly Arg Glu Glu Ser Arg Glu
                85                  90                  95

Pro Val Pro Glu Ser Pro Lys Pro Ala Gly Val Glu Ile Arg Ser Ala
            100                 105                 110

Thr Gly Lys Glu Val Leu Gln Asn Leu Gly Pro Lys Asp Lys Glu Phe
        115                 120                 125

Val Met Asn Pro Ala Asn Ala Gln Gly Arg His Thr Pro Gly Thr Arg
    130                 135                 140

Leu Leu
145
```

<210> SEQ ID NO 9
<211> LENGTH: 51
<212> TYPE: DNA
<213> ORGANISM: Rattus norvegicus

<400> SEQUENCE: 9

```
gtgatgaatc ccgcaaacgc gcaaggcaga catacacccg gtaccagact c               51
```

<210> SEQ ID NO 10
<211> LENGTH: 432
<212> TYPE: DNA
<213> ORGANISM: Rattus norvegicus

<400> SEQUENCE: 10

```
ggatccatgg cttcgggccg aaggggttgg gacagctccc acgaggacga cctgcctgtg      60
```

-continued

```
tacttggccc ggccgggcac cacagatcag gtcccacggc agaagtacgg tggcatgttc    120
tgcaacgtgg agggcgcctt cgagagcaag acattggatt ttgatgccct gagtgtggga    180
cagcgcggcg ccaaaactcc ccggagcagc cagggcagcg gccgcggcgc ggggaaccgg    240
cccggggtgg aagggacac gcgcaggggc ccgggccggg aggagagcag ggagcccgtg     300
cctgagtcgc ccaagcccgc cggggtagag atccggagcg ccactggcaa ggaggtcttg    360
cagaacctcg gtcccaagga caaggaattc gcagccgttc ttctccctgt tcttcttgcc    420
gcacccctcg ag                                                       432
```

<210> SEQ ID NO 11
<211> LENGTH: 142
<212> TYPE: PRT
<213> ORGANISM: Rattus norvegicus

<400> SEQUENCE: 11

```
Met Ala Ser Gly Arg Arg Gly Trp Asp Ser Ser His Glu Asp Asp Leu
1               5                   10                  15

Pro Val Tyr Leu Ala Arg Pro Gly Thr Thr Asp Gln Val Pro Arg Gln
            20                  25                  30

Lys Tyr Gly Gly Met Phe Cys Asn Val Glu Gly Ala Phe Glu Ser Lys
        35                  40                  45

Thr Leu Asp Phe Asp Ala Leu Ser Val Gly Gln Arg Gly Ala Lys Thr
    50                  55                  60

Pro Arg Ser Ser Gln Gly Ser Gly Arg Gly Ala Gly Asn Arg Pro Gly
65                  70                  75                  80

Val Glu Gly Asp Thr Arg Arg Gly Pro Gly Arg Glu Glu Ser Arg Glu
                85                  90                  95

Pro Val Pro Glu Ser Pro Lys Pro Ala Gly Val Glu Ile Arg Ser Ala
            100                 105                 110

Thr Gly Lys Glu Val Leu Gln Asn Leu Gly Pro Lys Asp Lys Glu Phe
        115                 120                 125

Ala Ala Val Leu Leu Pro Val Leu Leu Ala Ala Pro Leu Glu
    130                 135                 140
```

<210> SEQ ID NO 12
<211> LENGTH: 36
<212> TYPE: DNA
<213> ORGANISM: Rattus norvegicus

<400> SEQUENCE: 12

```
gcagccgttc ttctccctgt tcttcttgcc gcaccc                              36
```